(12) United States Patent
Barthe et al.

(10) Patent No.: US 8,857,438 B2
(45) Date of Patent: Oct. 14, 2014

(54) DEVICES AND METHODS FOR ACOUSTIC SHIELDING

(75) Inventors: Peter G. Barthe, Phoenix, AZ (US); Michael H. Slayton, Tempe, AZ (US); Charles D. Emery, Scottsdale, AZ (US)

(73) Assignee: Ulthera, Inc., Mesa, AZ (US)

( * ) Notice: Subject to any disclaimer, the term of this patent is extended or adjusted under 35 U.S.C. 154(b) by 457 days.

(21) Appl. No.: 13/291,312

(22) Filed: Nov. 8, 2011

(65) Prior Publication Data

US 2012/0111339 A1    May 10, 2012

Related U.S. Application Data

(60) Provisional application No. 61/411,251, filed on Nov. 8, 2010.

(51) Int. Cl.
*A61F 13/00* (2006.01)
(52) U.S. Cl.
USPC .......................................... 128/846; 128/857
(58) Field of Classification Search
USPC .......................................... 128/846, 849–857
See application file for complete search history.

(56) References Cited

U.S. PATENT DOCUMENTS

| | | | |
|---|---|---|---|
| 2,427,348 A | 9/1947 | Bond et al. | |
| 3,913,386 A | 10/1975 | Saglio | |
| 3,965,455 A | 6/1976 | Hurwitz | |
| 3,992,925 A | 11/1976 | Perilhou | |
| 4,039,312 A | 8/1977 | Patru | |
| 4,059,098 A | 11/1977 | Murdock | |
| 4,101,795 A | 7/1978 | Fukumoto | |
| 4,166,967 A | 9/1979 | Benes et al. | |
| 4,211,948 A | 7/1980 | Smith et al. | |
| 4,211,949 A | 7/1980 | Brisken et al. | |
| 4,213,344 A | 7/1980 | Rose | |
| 4,276,491 A | 6/1981 | Daniel | |

(Continued)

FOREIGN PATENT DOCUMENTS

| | | |
|---|---|---|
| DE | 4029175 | 3/1992 |
| DE | 10140064 A1 | 3/2003 |

(Continued)

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

(Continued)

*Primary Examiner* — Michael A. Brown
(74) *Attorney, Agent, or Firm* — Knobbe, Martens, Olson & Bear, LLP

(57) ABSTRACT

Acoustic shielding system and method for protecting and shielding non-targeted regions or tissues that are not intended to be treated by ultrasonic procedures from acoustic energy using a shield. In some embodiments, the shield comprises multiple layers made of one or more materials with one or more acoustic impedances. In some embodiments a multilayered shield includes materials with relatively different acoustic impedance levels. In some embodiments, the shield includes active components such as energy diversion devices, heating, cooling, monitoring, and/or sensing. In some embodiments, the shield is configured to protect an eye, mouth, nose or ear while allowing the ultrasound to treat the surrounding tissue. One embodiment of an eye shield is configured to fit under at least one eyelid and over a portion of the eye.

17 Claims, 11 Drawing Sheets

(56) References Cited

U.S. PATENT DOCUMENTS

| | | |
|---|---|---|
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Jaworski |
| 4,973,096 A | 4/1990 | Jaworski |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,988 A | 12/1995 | Fujio |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |

(56) References Cited

U.S. PATENT DOCUMENTS

| | | |
|---|---|---|
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,882 A | 11/1999 | Rosenschein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe |
| 6,039,048 A | 3/2000 | Silberg |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |

(56) References Cited

U.S. PATENT DOCUMENTS

| | | |
|---|---|---|
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Constantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,572,552 B2 | 6/2003 | Fukukita |
| 6,595,934 B1 | 7/2003 | Hissong |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 | 12/2003 | Miller |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laugharn, Jr. et al. |
| 6,719,694 B2 | 4/2004 | Weng |
| 6,726,627 B1 | 4/2004 | Lizzi et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,327,071 B2 * | 2/2008 | Nishiyama et al. ....... 310/313 A |
| 7,331,951 B2 | 2/2008 | Eshel et al. |
| 7,332,985 B2 * | 2/2008 | Larson et al. ................. 333/187 |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 | 11/2010 | Barthe |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,955,281 B2 | 6/2011 | Pedersen et al. |

(56) References Cited

U.S. PATENT DOCUMENTS

| | | |
|---|---|---|
| 7,967,764 B2 | 6/2011 | Lidgren et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,726,781 B2 * | 5/2014 | Eckhoff et al. .............. 89/36.05 |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193831 A1 | 12/2002 | Smith |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041880 A1 | 3/2004 | Ikeda et al. |
| 2004/0042168 A1 | 3/2004 | Yang et al. |
| 2004/0049134 A1 | 3/2004 | Tosaya et al. |
| 2004/0059266 A1 | 3/2004 | Fry |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 * | 5/2005 | Larson et al. ................ 333/191 |
| 2005/0113689 A1 | 5/2005 | Gritzky |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli et al. |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0228281 A1 | 10/2005 | Nefos |
| 2005/0240170 A1 | 10/2005 | Zhang et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |

(56) References Cited

U.S. PATENT DOCUMENTS

| | | |
|---|---|---|
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0238994 A1 | 10/2007 | Stecco et al. |
| 2007/0239075 A1 | 10/2007 | Rosenberg |
| 2007/0239079 A1 | 10/2007 | Manstein et al. |
| 2007/0239142 A1 | 10/2007 | Altshuler |
| 2008/0027328 A1 | 1/2008 | Klopotek |
| 2008/0039724 A1 | 2/2008 | Seip et al. |
| 2008/0071255 A1 | 3/2008 | Barthe |
| 2008/0366220 | 3/2008 | Makin et al. |
| 2008/0086054 A1 | 4/2008 | Slayton |
| 2008/0097253 A1 | 4/2008 | Pedersen et al. |
| 2008/0139974 A1 | 6/2008 | Da Silva |
| 2008/0167556 A1 | 7/2008 | Thompson |
| 2008/0183077 A1 | 7/2008 | Moreau-Gobard et al. |
| 2008/0188745 A1 | 8/2008 | Chen et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0012394 A1 | 1/2009 | Hobelsberger et al. |
| 2009/0043293 A1 | 2/2009 | Pankratov et al. |
| 2009/0069677 A1 | 3/2009 | Chen et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0318909 A1 | 12/2009 | Debenedictis et al. |
| 2010/0011236 A1 | 1/2010 | Barthe et al. |
| 2010/0022919 A1 | 1/2010 | Peterson |
| 2010/0022922 A1 | 1/2010 | Barthe et al. |
| 2010/0042020 A1 | 2/2010 | Ben-Ezra |
| 2010/0049178 A1 | 2/2010 | Deem et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Makin et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 A2 | 12/1989 |
| EP | 1479412 A1 | 11/1991 |
| EP | 0473553 | 4/1992 |

(56) References Cited

FOREIGN PATENT DOCUMENTS

| | | |
|---|---|---|
| EP | 0661029 A1 | 7/1995 |
| EP | 1050322 A1 | 11/2000 |
| EP | 1234566 | 8/2002 |
| EP | 1262160 | 12/2002 |
| EP | 1374944 | 1/2004 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 4-150847 | 5/1992 |
| JP | 04150847 | 5/1992 |
| JP | 7080087 | 3/1995 |
| JP | 07505793 | 6/1995 |
| JP | 2007505793 | 6/1995 |
| JP | 7222782 | 8/1995 |
| JP | 1997047458 | 2/1997 |
| JP | 9503926 | 4/1997 |
| JP | 11-505440 | 5/1999 |
| JP | 11-506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002-537939 | 11/2002 |
| JP | 2003050298 | 2/2003 |
| JP | 2003204982 | 7/2003 |
| JP | 2004-147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2009518126 | 5/2009 |
| JP | 2010517695 | 5/2010 |
| KR | 1020010024871 | 3/2001 |
| KR | 100400870 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| WO | WO 96/25888 | 8/1996 |
| WO | WO 96/39079 | 12/1996 |
| WO | WO 9735518 | 10/1997 |
| WO | WO 9832379 | 7/1998 |
| WO | WO 9933520 | 7/1999 |
| WO | WO 9949788 | 10/1999 |
| WO | WO 0006032 | 2/2000 |
| WO | WO 0015300 | 3/2000 |
| WO | WO 0021612 | 4/2000 |
| WO | WO 0053113 | 9/2000 |
| WO | WO 0128623 | 4/2001 |
| WO | WO 0182777 | 11/2001 |
| WO | WO 0182778 | 11/2001 |
| WO | WO 0187161 | 11/2001 |
| WO | WO 0209813 | 2/2002 |
| WO | WO 0224050 | 3/2002 |
| WO | WO 02024050 | 3/2002 |
| WO | WO 02092168 | 11/2002 |
| WO | WO 03/053266 | 7/2003 |
| WO | WO 03/006547 | 8/2003 |
| WO | WO 03065347 | 8/2003 |
| WO | WO 03070105 | 8/2003 |
| WO | WO 03077833 | 9/2003 |
| WO | WO 03086215 | 10/2003 |
| WO | WO 03/096883 A2 | 11/2003 |
| WO | WO 03/099382 | 12/2003 |
| WO | WO 03099177 | 12/2003 |
| WO | WO 03101530 | 12/2003 |
| WO | WO 04000116 | 12/2003 |
| WO | WO 2004080147 | 9/2004 |
| WO | WO 2004110558 | 12/2004 |
| WO | WO 2005065408 | 7/2005 |
| WO | WO 2005090978 | 9/2005 |
| WO | WO 2006036870 | 4/2006 |
| WO | WO 2006042168 | 4/2006 |
| WO | WO 2006042201 | 4/2006 |
| WO | WO 2006065671 | 6/2006 |
| WO | WO 2006082573 | 8/2006 |
| WO | WO 2007067563 | 6/2007 |
| WO | WO 2008036622 | 3/2008 |
| WO | WO 2009013729 | 1/2009 |
| WO | WO2009/149390 | 10/2009 |

OTHER PUBLICATIONS

Arthur et al., "Non-invasive estimation of hyperthermia temperatures with ultrasound," Int. J. Hyperthermia, Sep. 2005, 21(6), pp. 589-600.
Barthe et al., "Ultrasound therapy system and ablation results utilizing miniature imaging/therapy arrays," Ultrasonics Symposium, 2004 IEEE, Aug. 23, 2004, pp. 1792-1795, vol. 3.
Chen, L. et al., "Effect of Blood Perfusion on the ablation of liver parenchyma with high intensity focused ultrasound," Phys. Med. Biol; 38:1661-1673; 1993b.
Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Decision of the Korean Intellectual Property Tribunal dated Jun. 28, 2013 regarding Korean Patent No. 10-1142108, which is related to the pending application and/or an application identified in the Table on pp. 2-4 of the Information Disclosure Statement herein (English translation, English translation certification, and Korean decision included).
Fry, W.J. et al., "Production of Focal Destructive Lesions in the Central Nervous System with Ultrasound," J. Neurosurg., 11:471-478; 1954.
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Haar, G.R. et al., "Tissue Destruction with Focused Ultrasound in Vivo," Eur. Urol. 23 (suppl. 1):8-11; 1993.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Husseini et al, "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Pluronic micelles," BMD Cancer 2002, 2:20k, Aug. 30, 2002, pp. 1-6.
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.

(56) References Cited

OTHER PUBLICATIONS

Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).

Madersbacher, S. et al., "Tissue Ablation in Benign Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Confirmed Bulk Ablation and Therapy Monitoring Using Intracorporeal Image-Treat Ultrasound Arrays," 4th International Symposium on Therapeutic Ultrasound, Sep. 19, 2004.

Makin et al., "Miniaturized Ultrasound Arrays for Interstitial Ablation and Imaging," UltraSound Med. Biol. 2005, Nov. 1, 2005, pp. 1539-1550, vol. 31(11).

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling and Experiments," J. Acoust. Soc. Am., Oct. 1, 2005, pp. 2715-2724, vol. 118(4).

Mitragotri, S., "Healing sound: the use of ultrasound in drug delivery and other therapeutic applications," Nature Reviews; Drug Delivery, pp. 255-260, vol. 4 (Mar. 2005).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N.T., et al., "Transrectal Ablation of Prostrate Tissue Using Focused Ultrasound," 1993 Ultrasonics Symposium, IEEE, pp. 1207-1210.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med. & Biol. vol. 19, No. 2, pp. 123-125 (1993).

Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.

White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.

* cited by examiner

FIG. 3

| Material | Impedance multiple of air |
|---|---|
| Air | 1 |
| Aluminum | 42,500 |
| Alumina Oxide | 80,000 |
| Beryllium | 57,500 |
| Boron Carbide | 66,000 |
| Brass | 91,750 |
| Cadmium | 60,000 |
| Copper | 104,000 |
| Glass (crown) | 47,250 |
| Glycerin | 6,050 |
| Gold | 156,500 |
| Ice | 8,750 |
| Inconel | 118,000 |
| Iron | 113,500 |
| Iron (cast) | 83,000 |
| Lead | 61,500 |
| Magnesium | 25,000 |
| Mercury | 49,000 |
| Molybdenum | 160,500 |
| Monel | 119,000 |
| Neoprene | 5,250 |
| Nickel | 123,750 |
| Nylon, 6-6 | 7,250 |
| Oil (SAE 30) | 3,750 |
| Platinum | 174,500 |
| Plexiglass | 7,750 |
| Polyethylene | 4,250 |
| Polystyrene | 6,250 |
| Polyurethane | 4,750 |
| Quartz | 38,000 |
| Rubber, Butyl | 5,000 |
| Silver | 95,000 |
| Steel, mid | 115,000 |
| Steel, stainless | 113,500 |
| Teflon | 7,500 |
| Tin | 60,500 |
| Titanium | 68,250 |
| Tungsten | 252,500 |
| Uranium | 157,500 |
| Water | 3,700 |
| Zinc | 74,000 |

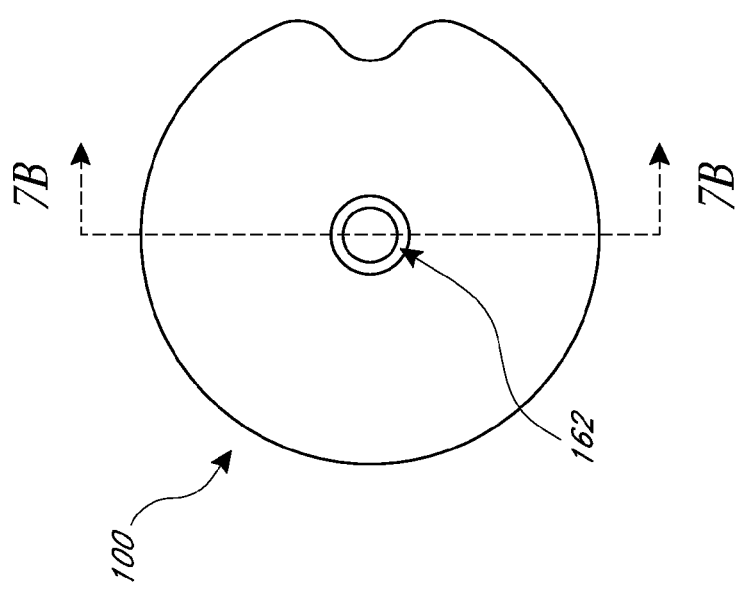
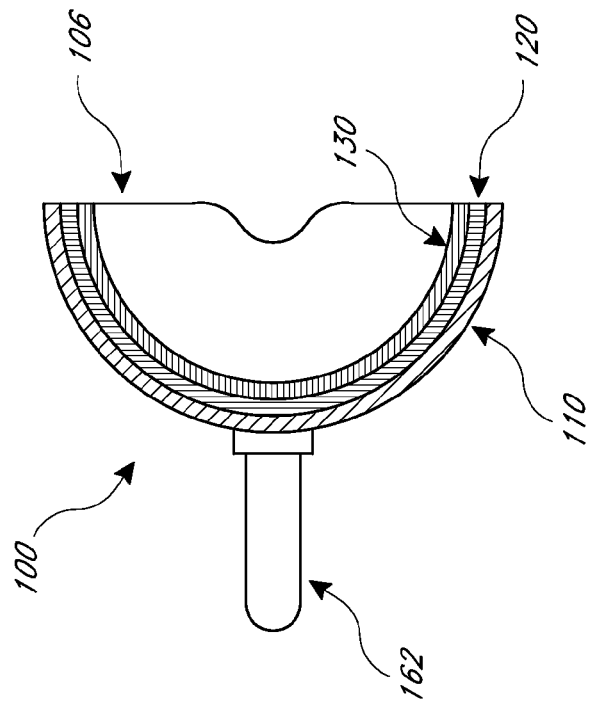

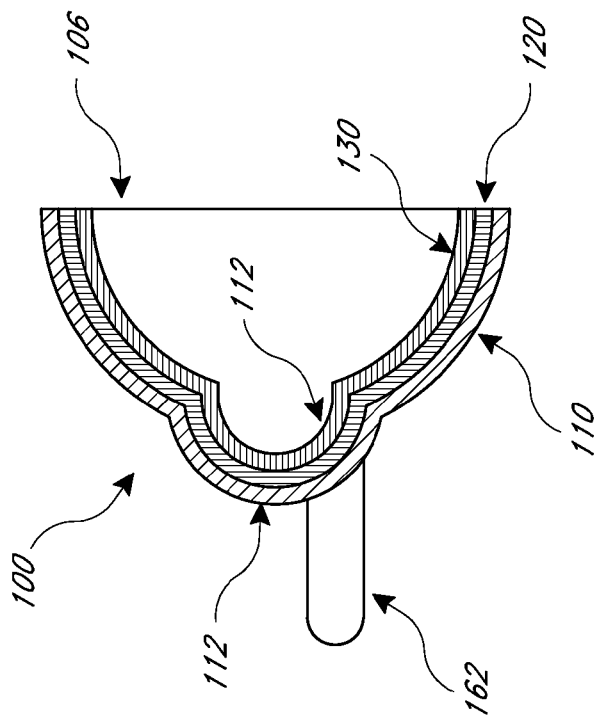
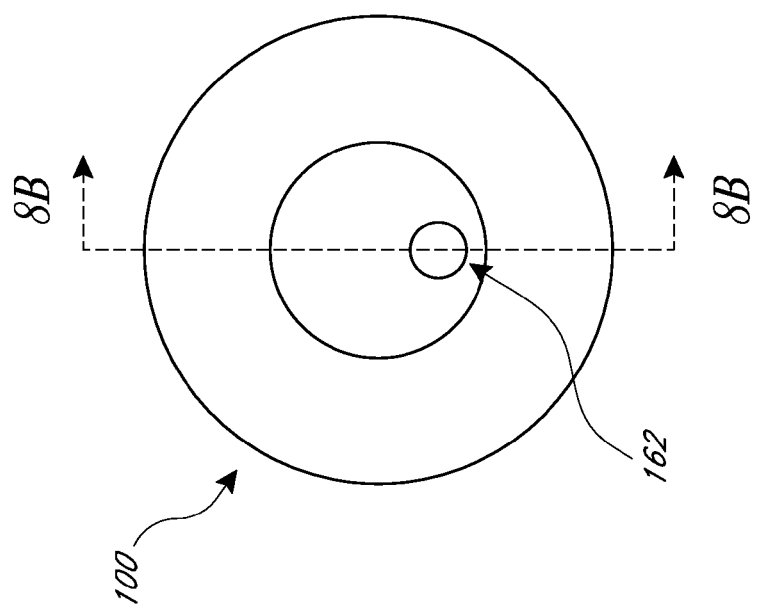
FIG. 8B
FIG. 8A

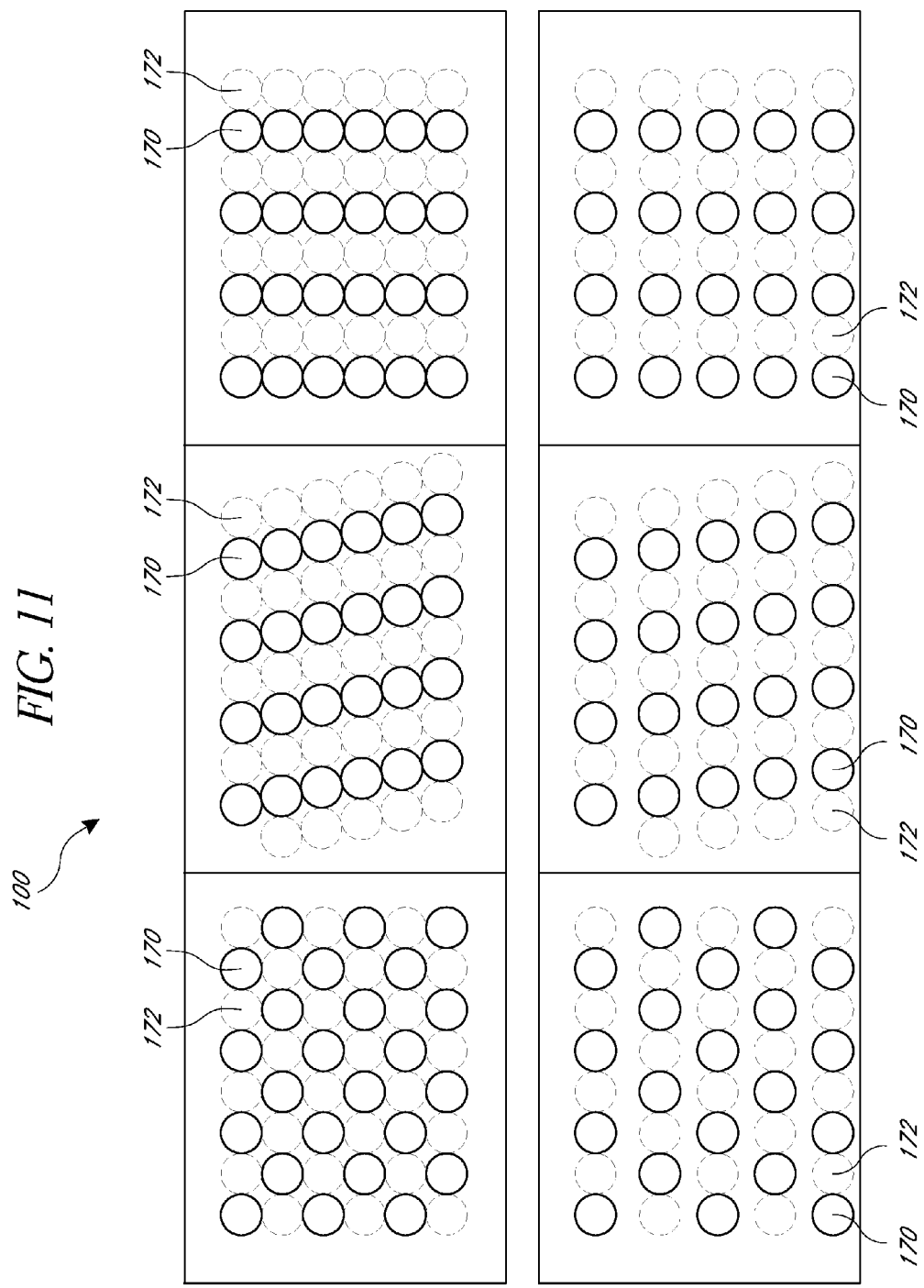

EXPERIMENTAL RESULTS

| ULTRASONIC TRANSDUCER | ACOUSTIC POWER MEASURED | | HYDROPHONE TRANSMISSION |
|---|---|---|---|
| | NO SHIELD | SHIELD | |
| 7.5MHz - 3.0mm | 15.6w (100%) | 0.0 (0%) | <-56dB* |
| 10.5MHz - 2.0mm | 14.6w (100%) | 0.0 (0%) | <-56dB* |

RESOLUTION +/- 150 mW       * LESS THAN 2.5ppm (PARTS PER MILLION)

DEVICES AND METHODS FOR ACOUSTIC SHIELDING

CROSS-REFERENCE TO RELATED APPLICATIONS

This application claims the benefit of priority from U.S. Provisional Application No. 61/411,251 filed on Nov. 8, 2010, which is incorporated by reference in its entirety herein.

BACKGROUND

1. Field

Embodiments of the present invention generally relate to systems and methods for performing various treatments and/or imaging procedures safely and effectively by focusing on targeted tissue while shielding or protecting a non-targeted region. Cosmetic eye shields are provided in several embodiments.

2. Description of the Related Art

In certain instances, eye shields can protect a patient's eyes during various surgical procedures in which scalpels, electrocauterizers or lasers are used to carry out the surgical procedures. Some eye shields protect the eyes from direct exposure to intense light from a light source during eye surgery, or from electron beams during electron beam treatment of eyelid tumors. However, such shields generally do not sufficiently protect the eyes, other non-target regions, such as, tissues, body parts, organs, medical devices, or medical implants from acoustic energy during an ultrasound treatment or imaging procedure.

SUMMARY

In several embodiments, the invention comprises a shield for use in energy-based therapeutic or imaging applications, in which the shield reduces energy transmission to non-target regions. Non-target regions include, but are not limited to, tissue and synthetic implants. In some embodiments, therapeutic ultrasound treatment (e.g., cosmetic enhancement) and/or imaging procedures are intended to affect targeted tissue. While the acoustic energy of ultrasound treatment or imaging procedures may be highly focused and localized in the targeted tissues or parts of the body often there exists residual acoustic energy levels beyond the focal point or outside the treatment or imaging region during these procedures. In some embodiments, it is necessary or desirable to protect or shield certain tissues, parts of the body, organs, medical devices, and/or medical implants not intended to be treated and/or imaged from acoustic energy during these ultrasound procedures. In various embodiments, acoustic transmission can be reduced by a shield through reflection, absorption, and/or diffraction. For example, according to one embodiment, it is desirable to protect the eyes from high levels of acoustic energy if a patient is undergoing enhancement procedures on, near, or around the eyelids.

There is a need for devices and procedures for protecting certain tissues, body parts, organs, medical devices, and/or medical implants from high levels of acoustic energy during an ultrasound treatment (e.g., cosmetic enhancement) and/or imaging procedure while permitting intended procedures on targeted tissue. In addition, there is a need for devices and procedures that meet the regulatory requirements for protection from unintended ultrasound exposure.

In various embodiments, a shield for protecting part of a subject's body from undesired exposure to acoustic energy is provided. In various embodiments, a shield can block, reduce, eliminate, redirect, absorb, convert, reflect, diffract, deflect, divert, disperse and/or reroute acoustic energy. In some embodiments, a shield is configured to protect an eye from exposure to acoustic energy. In some embodiments, a shield is configured to protect tissue from heating of the shield in absorbing or deflecting acoustic energy. In various embodiments, a shield is configured to address a thermal component of shielding acoustic energy. For example, in one embodiment, acoustic energy is blocked by a shield that absorbs some of the acoustic energy. In one embodiment, the shield reflects some or none of the acoustic energy. In some embodiments, acoustic energy may be converted to heat or electrical energy through a piezoelectric effect. In some embodiments, the shield includes an absorbing material with a high heat capacity, such that more energy is needed to raise the temperature of the absorber. In various embodiments, a shield reduces the thermal conductivity to surrounding tissue by absorbing with a high heat capacity, or by routing the heat away from the tissue through an energy diversion device. In some embodiments, the energy diversion device is an energy dispersion device, an electrical circuit, a heat conduit, a coolant channel, a heat exchanger, and/or a fluid configured to draw excess heat or energy from a shield. In some embodiments, a shield is configured for protecting tissue from undesired exposure to acoustic energy. In some embodiments, a shield is configured for protecting tissue from undesired exposure to acoustic energy as well as the potential heat generated from the acoustic energy.

In some embodiments, a multi-layered eye shield is configured for protecting a subject's eye from undesired exposure to acoustic energy. In some embodiments, the shield comprises at least a first layer, a second layer and a third layer. In one embodiment, the first and third layers are stainless steel, and the second (middle) layer is air. The first and third layers can be the same material or can be made of different materials. The middle layer and the outer layers have differential acoustic impedances in several embodiments. In various embodiments, the acoustic impedance ratio between two adjacent layers of the shield is at least 1,000:1, or 10,000:1, 50:000:1, or 100,000:1, or 250,000:1, or, 500,000:1, or 1,000,000:1, or 10,000,000:1, or approaching infinity, or infinite.

In one embodiment, the invention comprises a biocompatible shield that is configured to be sufficiently thin to fit under a patient's eyelids to protect the patient's eyes from high levels of acoustic energy while allowing the patient's eyelids or other tissues surrounding the eyes to be affected as intended during a cosmetic enhancement and/or imaging procedure. In various embodiments, a biocompatible shield is configured for use in protecting the eye from ultrasound energy during a blepharoplasty procedure. In various embodiments, the biocompatible shield may include one or more manipulation devices, handles, pinch grip, levers, suction devices, magnetic handles, or other similar gripping devices to aid in the placement and removal of the biocompatible shield from the patient's eyes. In various embodiments, the manipulation device is coupled, permanently coupled, temporarily coupled, and/or removably coupled to the shield. In one embodiment the manipulation device includes a tool that is detachable from the shield.

In some embodiments, the invention comprises a shield for protecting other body parts from ultrasonic exposure. Accordingly, several embodiments of the present invention provide an acoustic shielding system and a method for protecting and shielding certain tissues from levels of acoustic energy. In various embodiments, the acoustic shielding system includes a biocompatible shield interposed between an acoustic treatment system and non-target tissue that is not intended to be treated in order to shield the non-target tissue from acoustic energy.

A shield, according to one embodiment, comprises materials that provide high attenuation and/or acoustic impedance. In some embodiments, shields are made of materials that provide different or significantly different levels of attenuation and/or acoustic impedance. In various embodiments, shield materials have a reflection coefficient, wherein a reflection coefficient of 100% corresponds to complete reflection of energy, or 100% reflection. In various embodiments, shield materials have a reflection coefficient that is in a range of 10-100%, 25-100%, 50-100%, 60-100%, 65-100%, 70-100%, 75-100%, 80-100%, 85-100%, 90-100%, 95-100% or more. In some embodiments, the shields, and procedures thereof, may be configured to protect certain tissues, body parts, organs, medical devices, and/or medical implants from non-invasive or minimally invasive procedures employing energy, such as, for example, acoustic, ultrasound, laser, radiation, thermal, cryogenic, electron beam, photon-based, magnetic resonance or combinations thereof.

In several embodiments of the invention, one or more shields are used in non-invasive or minimally invasive procedures involving one or more of ultrasound, fluoroscopy, radiation (e.g., microwave) light, lasers, electricity, magnetic (e.g., magnetism, magnetic resonance) heating, and cooling. In one embodiment, one or more shields are used to shield a non-target region from the combined use of ultrasound energy and photon-based energy. In several embodiments, one or more shields are used to shield a non-target region from the combined use of ultrasound energy and at least one other energy, applied simultaneously or individually. For example, one or more shields may be used in procedures using combinations of ultrasound and laser, ultrasound and IPL (intense pulse light), ultrasound and radiofrequency, or ultrasound and magnetic energy. In one embodiment, non-metallic shields are used when procedures employ radiofrequency or magnetic energy (alone, together or in combination with ultrasound). In some embodiments, a shield is configured to shield non-target regions from at least one of two (or more) energy sources. For example, in combined therapies, a shield may shield against both ultrasound and photon-based energy, or may shield only ultrasound energy and not photon-based energy. In some embodiments of the invention, one or more shields, as disclosed herein, are used for focusing, reflecting and/or concentrating energy. The energy may comprise one or more of ultrasound, fluoroscopy, radiation, light, laser, photon-based, electricity, magnetic, heating, or cooling energy. In one embodiment, a shield is used to reflect energy (for example, for imaging and/or therapy procedures) into body cavities or tortuous pathways where direct application of the energy may be difficult or undesired. One or more shields may also be used to concentrate energy. In one embodiment, the shield comprises one or more concave or curved surfaces configured for concentrating energy. In some embodiments, one or more shields are provided to focus ultrasound energy, photon-based energy or a combination of the two energies to a target region.

In various embodiments, the biocompatible shield includes multiple layers and/or materials. In one embodiment, one or more layers of material are air. In one embodiment, one or more layers of material are separated by a layer of air. In one embodiment, one or more layers include a vacuum or near vacuum. In various embodiments, the biocompatible shield includes a plurality of layers, multiple shields and/or components.

In various embodiments, a shield configured for selectively protecting a non-target region from acoustic energy includes a first layer and a second layer. The first layer includes at least a first material with a first acoustic impedance. The second layer is in contact with and adjacent to the first layer. The second layer includes at least a second material with a second acoustic impedance. In one embodiment, the first acoustic impedance is at least ten times the second acoustic impedance. In one embodiment, the first layer and the second layer are configured to reduce acoustic transmission to a non-target region in a body of a patient.

In one embodiment, the shield includes one or more surface features configured for a high reflection coefficient. In one embodiment, one or more features produce an air pocket between the shield and tissue. In one embodiment, one or more features include a concave, a convex, or both concave and convex features.

In various embodiments, the shield configured for selectively protecting tissue from acoustic energy can also include a third layer with at least a third material in contact with and adjacent to the second layer. The third material has a third acoustic impedance. In one embodiment, the third acoustic impedance is at least ten thousand times the second acoustic impedance. In various embodiments, the first acoustic impedance is at least one hundred times, at least one thousand times, at least fifty thousand times, and/or at least one hundred thousand times, the second acoustic impedance. In some embodiments, the shield is made at least partially of stainless steel. In some embodiments, the second layer is sealed between the first layer and the third layer. In one embodiment, the first layer is stainless steel, the second layer is air, and the third layer is stainless steel. In another embodiment, the first layer is stainless steel, the second layer is a partial vacuum, and the third layer is stainless steel.

In some embodiments, the shield is configured to fit over a portion of an eye and underneath at least one eyelid. In one embodiment, a therapeutic substance, which can at least one of protect the eye and facilitate in keeping the eye moist, is coated on the layer in contact with the eye. In one embodiment, the shield comprises a source of a saline solution, which can facilitate in keeping the eye moist. In one embodiment, the shield includes an optional manipulation device to aid in the insertion and removal of the shield from the body of a patient.

In various embodiments, an eye shield is configured for selectively protecting the eye from acoustic energy applied to surrounding tissue. The eye shield includes a first, second and third layer. The first layer is made of a first material with a first acoustic impedance. The second layer is in contact with and adjacent to the first layer. The second layer is made of a second material with a second acoustic impedance. In one embodiment, the first acoustic impedance is at least ten thousand times the second acoustic impedance. The third layer is made of a third material in contact with and adjacent to the second layer. The third material has a third acoustic impedance. In one embodiment, the third acoustic impedance is at least ten thousand times the second acoustic impedance. In various embodiments, the first layer, the second layer and the third layer are configured to be positioned over eye and to reduce delivery acoustic energy to the eye.

In one embodiment, a method of shielding the eye from an emission of ultrasound energy in a cosmetic enhancement procedure to the area around an eye includes the steps of positioning a shield between an eyelid and an eye and applying ultrasound energy from a transducer to tissue proximate the upper eyelid and the lower eyelid. In some embodiments, the shield includes a first layer with a first material with a first acoustic impedance, a second layer with a second material with a second acoustic impedance, and a third layer with a third material having a third acoustic impedance. In some embodiments, the second layer is in contact with and adjacent to the first layer. In some embodiments, the third layer is in contact with and adjacent to the second layer. In various embodiments, the first acoustic impedance is at least ten, hundred, thousand, ten thousand, one hundred thousand or more times the second acoustic impedance. In various embodiments, the third acoustic impedance is at least ten, hundred, thousand, ten thousand, one hundred thousand or more times the second acoustic impedance. In some embodiments, the first layer, the second layer and the third layer are configured to reduce acoustic transmission to the eye.

In one embodiment, a method of shielding a non-targeted region of a body from undesired emission of energy includes the steps of positioning a shield between a non-targeted region of the body a source of the energy and applying the energy to tissue proximate the non-targeted region of the body. The shield includes a first layer with a first acoustic impedance, a second layer with a second acoustic impedance, and a third layer with a third acoustic impedance. The second layer is in contact with the first layer and the third layer. The first acoustic impedance and the third acoustic impedance are at least one thousand times the second acoustic impedance. The first layer, the second layer and the third layer are configured to reduce application of the energy to the non-targeted region of the body. In various embodiments, the undesired energy comprises ultrasound energy, or comprises a combination of ultrasound energy and at least one other energy. In one embodiment, the method also includes applying energy from a transducer to tissue proximate the upper eyelid and the lower eyelid. In one embodiment, the method can further include applying the energy from a transducer to perform a cosmetic enhancement procedure, such as, for example, a face lift, a rhinoplasty procedure, or a blepharoplasty procedure.

Further areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein:

FIG. 3 is a table listing relative acoustic impedance of some materials compared to the acoustic impedance of air.

FIG. 7A is a schematic front view of an eye shield with an optional removable manipulation device according to one embodiment of the present invention.

FIG. 7B is a schematic, partial cross-sectional side view of the eye shield of FIG. 7A.

FIG. 8A is a schematic front view of an eye shield with an optional removable manipulation device according to one embodiment of the present invention.

FIG. 8B is a schematic, partial cross-sectional side view of the eye shield of FIG. 8A.

FIG. 11 is a schematic, front view of a shield according to various embodiments of the present invention.

DETAILED DESCRIPTION

Figure 1:
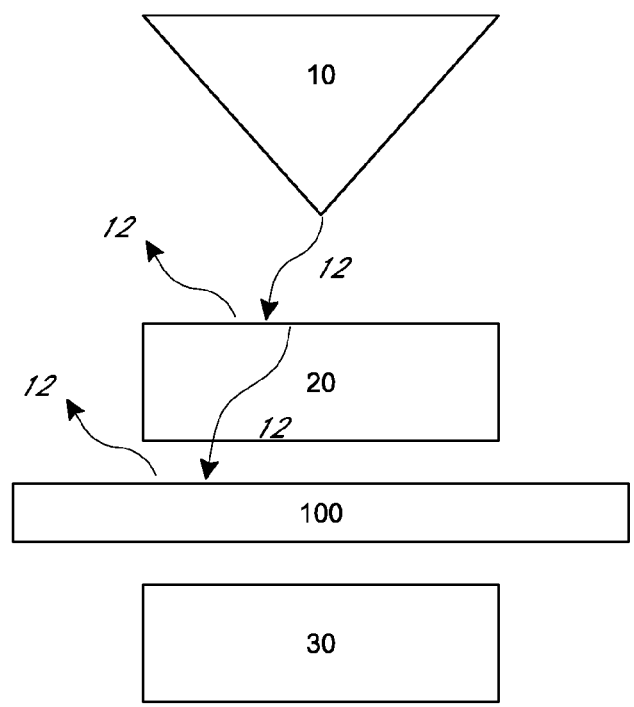
FIG. 1 is a schematic block diagram illustrating a shielding system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

FIG. 1 illustrates one embodiment of the invention in which a shield 100 is configured to reduce or eliminate exposure of non-target region 30 from energy 12 emitted from a procedure system 10 intended for target tissue 20. In various embodiments, the shield 100 is biocompatible and configured to shield and/or protect tissues, body parts, organs, medical devices, implants, and/or material in the body of a patient that are not intended to be treated, enhanced, and/or imaged during various procedures. In various embodiments, a procedure system 10 configured to emit energy 12 to affect target tissue 20. In various embodiments, a procedure system 10 is any one or more of a cosmetic enhancement system, a medical system, a sensor system, a diagnostic system, an imaging system, a visualization system, a monitoring system, a treatment system, or combinations thereof. In various embodiments, a procedure system 10 can include, but is not limited to, ultrasound, fluoroscopy, laser, radiation, heating, cooling, electron beam, photon, magnetic resonance, magnetic, electric, focusing, concentrating, reflecting x-ray, and/or orthoscopic devices, systems or methods.

In various embodiments, a procedure system 10 can include at least one source that can provide ultrasound energy, photon based energy, thermal energy, RF energy, or combinations thereof. In one embodiment, a procedure system 10 can include a source that can provide ultrasound energy and a source that can provide a photon-based energy. In one embodiment, the source that can provide a photon-based energy can be a laser. Photon-based energy can be provided by various sources, such as, for example, a laser, intense pulsed light ("IPL"), an infrared source, an ultraviolet source, light emitting diodes ("LED"), or combinations thereof. In some embodiments, a procedure system 10 can focus energy provided by the source to one or more depths within targeted tissue 20. In one embodiment, the procedure system 10 is an ultrasound system. In various embodiments, the procedure system 10 is an ultrasound system configured for imaging, visualization, sensing, monitoring, enhancing, and/or treating target tissue 20. In some embodiments, the procedure system 10 is configured for at least one of cosmetic enhancement and imaging of target tissue 20. In some embodiments, the procedure system 10 is configured for inducing a bio-effect to at least a portion of target tissue 20.

In various embodiments, target tissue 20 is tissue intended to be acted upon by emitted energy 12 from the procedure system 10. In various embodiments, target tissue 20 is, but is not limited to, any of skin, eyelids, eye lash, eye brow, caruncula lacrimalis, crow's feet, wrinkles, acne, sebaceous glands, eye, nose, mouth, tongue, teeth, gums, ears, brain, face, cheek, chin, jowls, neck, body, heart, lungs, ribs, abdomen, stomach, liver, kidneys, uterus, breast, prostrate, testicles, glands, thyroid glands, sweat glands, internal organs, hair, muscle, bone, ligaments, cartilage, fat, fat labuli, cellulite, subcutaneous tissue, implanted tissue, an implanted organ, lymphoid, a tumor, a cyst, an absence, or a portion of a nerve, or any combination thereof. In various embodiments, the emitted energy 12 from the procedure system 10 is partially or completely absorbed, reflected, refracted, converted or transmitted by or through target tissue 20. In some embodiments, the emitted energy 12 from the procedure system 10 can ablate a portion of target tissue 20. In some embodiments, the emitted energy 12 from the procedure system 10 can coagulate a portion of target tissue 20. In various embodiments, the emitted energy 12 from the procedure system 10 produces at least one of a thermal and a mechanical effect in target tissue 20. For example, a thermal effect can be creating a lesion in a portion of target tissue 20. For example, a mechanical effect can be cavitation. In some embodiments, the emitted energy 12 from the procedure system 10 can produce a bio-effect, such as, for example, increase blood perfusion to target tissue 20, induce collagen production in a portion of target tissue 20, minimize wrinkles above or in a portion of target tissue 20, rejuvenate skin above or in a portion of target tissue 20, or increase metabolization of fat in a portion of target tissue 20.

In various embodiments, the emitted energy 12 from the procedure system 10 can be applied to target tissue 20 in a non-invasive manner, or a minimally invasive manner, or combinations of both. A non-invasive manner can include applying the emitted energy 12 from a source from a surface above target tissue 20 and not damaging tissue between the surface and the target tissue 20. A minimally invasive manner can include applying the emitted energy 12 from a source below a surface above target tissue 20. A minimally invasive manner can include, a source coupled to or integrated with for example, a tool or catheter used in at least one of an endoscopic, a laparoscopic, and an orthoscopic procedures.

As shown schematically in FIG. 1, in one embodiment, a shield 100 can be placed between a procedure system 10 and a target tissue 20. In some embodiments, a shield 100 is configured to reflect some energy 12 back toward the target tissue 20. In one embodiment, target tissue 20 is intended for treatment with energy 12 directly form the procedure system 10 and reflected energy 12 from the shield 100 can be reduced or minimized with a material or structure as a part of, or separate from, shield 100. In one embodiment, a shield 100 may comprise a material or structure configured to block reflections of energy 12. In one embodiment, a shield 100 may have a separate material or structure configured to block reflections of energy 12 that is placed between the shield 100 and target tissue 20 and/or non-target region 30.

In various embodiments, non-target region 30 is not intended to be acted upon the emitted energy 12 from the procedure system 10. In various embodiments, non-target region 30 is any non-targeted tissue. In various embodiments, non-target region 30 is, but is not limited to, any of skin, eyelids, eye lash, eye brow, caruncula lacrimalis, crow's feet, wrinkles, eye, nose, mouth, tongue, teeth, gums, ears, brain, face, cheek, chin, jowls, neck, body, heart, lungs, ribs, abdomen, stomach, liver, kidneys, uterus, testicles, prostate, breast, glands, thyroid glands, sweat glands, internal organs, hair, muscle, bone, ligaments, cartilage, fat, fat labuli, cellulite, subcutaneous tissue, implanted tissue, an implanted organ, lymphoid, a tumor, a cyst, an absence, a portion of a nerve, an implant, a medical device, or any combination thereof.

In various embodiments, non-target region 30 is not a tissue. For example, the non-target region 30 may be an implant or material, such as for example, a pace maker, a hearing aid, dentures, a glucose monitor, a drug delivery system, a crown, a filling, a prosthetic body part, a stent, a screw, a plate, or any other such medical device, material or implant. For example, if target tissue 20 is a portion of a lung, a pace maker can be a non-target region 30, which can be protected from emitted energy 12 by shield 100 to prevent interference with and/or damage to the pace maker.

For example, in one embodiment, one or more shields 100 are used to protect non-target region 30 while ultrasound energy (or other energy, alone or combined with ultrasound energy) is applied to joints or muscles. One or more shields 100 may also be used to protect non-target region 30 ultrasound energy (or other energy, alone or combined with ultrasound energy) is applied to malignant or benign tumors. In one embodiment, application of energy to a tumor for imaging or therapeutic purposes is performed in conjunction with at least one shield positioned inside the body, in order to partially, substantially, or fully protect healthy tissue in non-target region 30 from the application of energy. One or more shields 100 may also be used to protect tissue during application of ultrasound energy (or other energy, alone or combined with ultrasound) to the oral, nasal or respiratory tracts. The shield 100 can be positioned inside the body or on an exterior surface of the body. In one embodiment, the shield 100 does not directly contact the body. In various embodiments, the shield 100 can to partially, substantially, or fully protect healthy tissue in non-target region 30.

In various embodiments, at least one shield 100 is configured to at least partially reduce, or completely eliminate emitted energy 12 from a procedure system 10 contacting or affecting a non-target region 30. In various embodiments, a shield 100 at least partially reflects, refracts, converts, cancels, and/or absorbs emitted energy 12. In accordance with various embodiments, systems and methods for tissue and/or implant shielding are configured to shield and/or protect certain tissues from high levels of acoustic energy during targeted ultrasound treatment and/or imaging procedures. In various embodiments, a shield can reduce energy transmission to an area of tissue to protect tissue from damage or to meet a regulatory threshold on energy transmission limits to a tissue, soft tissue, eye, etc. In various embodiments, a shield is configured to limit energy transmission to a tissue to a maximum of 1 watt per square centimeter (1000 mW/cm$^2$), 100 mW/cm$^2$, 90 mW/cm$^2$, 80 mW/cm$^2$, 70 mW/cm$^2$, 60 mW/cm$^2$, 50 mW/cm$^2$, 45 mW/cm$^2$, 40 mW/cm$^2$, 30 mW/cm$^2$, 25 mW/cm$^2$, 20 mW/cm$^2$, 10 mW/cm$^2$, 5 mW/cm$^2$ or less. In one embodiment, a biocompatible shield 100 is interposed between the procedure system 10 and non-target region 30. In some embodiments, the procedure system 10 is an ultrasound cosmetic enhancement and/or imaging system. In some embodiments, the procedure system 10 is an ultrasound treatment and/or imaging system.

In several embodiments, one or more shields are used to protect non-target regions during application of ultrasound energy or other energy (alone or in combination with ultrasound energy) to a target tissue 20. For example, one or more shields may be positioned inside the body to protect the liver, while endoscopic energy (e.g., ultrasound) is applied to the kidney. In one embodiment, at least one shield is coupled to a therapeutic delivery (or imaging) catheter. In some embodiments, the shield and the energy device are delivered in an integrated device. In other embodiments, the shield and energy device are delivered separately. Catheter-based percutaneous delivery systems to deliver one or more shields are provided in some embodiments.

In several embodiments, one or more shields are positioned inside a patient's body to partially or fully protect non-target region 30 tissue from energy exposure during a medical and/or cosmetic enhancement procedure on target tissue 20. In other embodiments, one or more shields are positioned to protect the practitioner (e.g., the doctor or the esthetician, or the procedure system operator) from energy exposure. For example, shields can be positioned to offer protection from the energy without contacting the practitioner, or may be positioned to contact the practitioner (e.g., flexible shielding material may be incorporated in protective coverings or gloves).

A shield according to several embodiments herein can block at least 25%, 50% 75%, 90% or 95% of energy from reaching the shielded area, such as, for example, at least a portion of non-target region 30. In one embodiment, the shield fully blocks all of the energy from reaching the shielded area.

One or more shields according to several embodiments herein are used not to shield regions from energy, but to concentrate, focus or direct energy into target tissue 20. In some embodiments, a single shield or multiple shields are provided to simultaneously shield certain non-target regions 30 while focusing energy into target tissue 20. One or more shields according to several embodiments herein are configured to convert energy from one form to another. One or more shields according to several embodiments herein are configured to re-radiate energy. One or more shields according to several embodiments herein are configured to re-radiate energy and create a focus from a secondary reflection.

Figure 2:
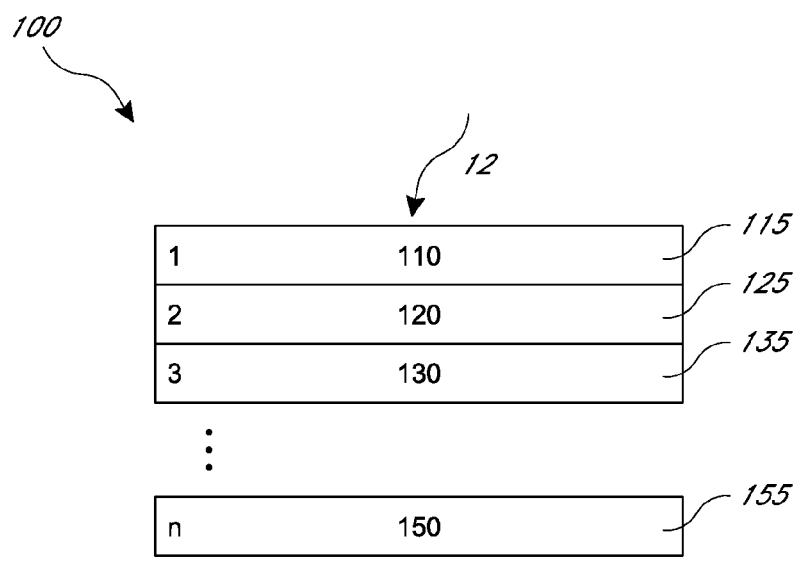
FIG. 2 is a schematic block diagram illustrating a shield with more than one layer according to various embodiments of the present invention.

As illustrated in FIG. 2, in accordance with various embodiments of a shield 100, the shield 100 includes one or more layers, such as, any of layer 110, 120, 130, and 150 comprise a material, such as any of material 115, 125, 135, and 155. In various embodiments, the shield 100 may comprise one, two, three, four, five, six, seven, eight, nine, ten, more than ten, twenty, fifty, less than one-hundred, one-hundred, or more than a hundred layers. In various embodiments, the layers can be made of the same material or a combination of different materials. As illustrated in FIG. 2, in various embodiments, the shield 100 can comprise a first layer 110 made of first material 115 that is adjacent and connected to a second layer 120 made of second material 125. In one embodiment, the shield 100 can comprise a third layer 130 made of third material 135 that is adjacent and connected to a second layer 120 made of second material 125. In various embodiments, the shield 100 can comprise any number of additional adjacent, connected layers 150 made of any number of materials 155 are also present, depending on the total number of layers in the shield 100. In various embodiments, the layers 110, 120, 130, 150 can be connected, attached, glued, adhered, painted, bonded, electronically dispersed and/or machined together. In various embodiments, layers may contact other layers with one or more layers in between. In one embodiment, a first layer 110 contacts a third layer 130, with a second layer 120 in between. In one embodiment, a second layer 120 can be sealed between a first layer 110 and a third layer 130. In various embodiments, the layers 110, 120, 130, 150 can comprise same or different materials 115, 125, 135, 155, characteristics, and/or properties.

In various embodiments, the one or more layers 110, 120, 130, 150 can be made of one or more materials 115, 125, 135, 155. In various embodiments, one or more layers 110, 120, 130, 150 is rigid, stiff, pliable, compliant, moldable, and/or flexible. In one embodiment, one or more layers 110, 120, 130, 150 can be a solid, liquid, gas, plasma or vacuum. In some embodiments, the individual layers may comprise composite materials that include various mixtures of solids, liquids, gases, plasmas, or voids at different ratios to obtain specific material characteristics. In one embodiment, one or more layers 110, 120, 130, 150 can be air. In one embodiment, one or more layers 110, 120, 130, 150 can be a vacuum or near vacuum, in which the respective density of the material relatively low or approaching zero density. In one embodiment, one or more layers 110, 120, 130, 150 has a pressure that is lower than atmospheric pressure, approaching a vacuum or complete a vacuum.

In various embodiments, the shield 100 can be made of, but is not limited to, various biocompatible materials and/or non-biocompatible materials. In various embodiments, any one material 115, 125, 135, 155 can be a metal or metal alloy, including, but not limited to, stainless steel, aluminum, beryllium, brass, cadmium, copper, iron, lead, magnesium, nickel, steel, titanium, tungsten, uranium, zinc, Nitinol, a precious metal, gold, silver, platinum, foil or other metal or metal alloy. In various embodiments, any one material 115, 125, 135, 155 can be a biocompatible ceramic, including, but not limited to, alumina, porcelain, hydroxyapatite, zirconia, or other ceramic. In various embodiments, materials 115, 125, 135, 155 can be any materials, including, but not limited to, plastics, polymers, silicones, epoxies, hydrogels, rubber, composites, thermoplastic elastomers, copolymers, copolyesters, polyamides, polyolefins, polyurethanes, vulcanizates, polyvinyl chloride, resins, fluropolymers, PTFE, FEP, ETFE, PFA, MFA, polycarbonate, acrylic, polypropylene, nylon, sulfone resins, synthetic materials, natural polymers, cellulose polymers, collagen, glass-reinforced materials, quartz, a silicate, a ceramic, or other materials. In various embodiments, any one material 125, 135, 155 can be a liquid, including but not limited to water, an alcohol, an oil, a gel, or mixtures thereof. In various embodiments, any one material 125, 135, 155 can be a gas, including but not limited to air, oxygen, nitrogen, a noble gas, helium, or mixtures thereof. In various embodiments, any one material 115, 125, 135, 155 can have one of the following characteristics hydrophilic, hydrophobic, anti-bacterial, conductive to heat, conductive to electricity, translucent to light, opaque to light, or combinations thereof. In various embodiments, any one material 115, 125, 135, 155 can be under a pressure, under a partial vacuum, or a vacuum.

In some embodiments, the shield 100 is made at least partially of stainless steel. In some embodiments, the second layer 120 is sealed between the first layer 110 and the third layer 130. In one embodiment, the first layer 110 is stainless steel, the second layer 120 is air, and the third layer 130 is stainless steel. In another embodiment, the first layer 110 is stainless steel, the second layer 120 is a partial vacuum, and the third layer 130 is stainless steel. In one embodiment, the first layer 110 is ceramic, the second layer 120 is air, and the third layer 130 is ceramic. In another embodiment, the first layer 110 is ceramic, the second layer 120 is a partial vacuum, and the third layer 130 is ceramic. These ceramic embodiments of the shield 100 can protect and/or shield non-target region 30 from a combination of emissions of two or more different types of energy, such as for example, but limited to, ultrasound energy and RF energy, or photon-based and RF energy, or ultrasound energy and photon-based energy.

In various embodiments, the shield 100 can be configured for one-time use, reuse, configure to be sterilizable, autoclavable, and/or washable. In one embodiment, the shield 100 can include a coating, such as, for example, an anti-bacterial coating. In one embodiment, the shield 100 can include a surface finish, such as, for example, a reflective surface, a smooth surface, a pitted surface, a sandblasted surface, a patterned surface, a surface with pockets, a surface with concave features, a surface with convex features, or other surface finishes. In some embodiments, the shield 100 can comprise a combination of metallic and non-metallic materials. For example, the shield 100 can comprise any number of metallic layers and a non-metallic layer is in contact with the patient to reduce or substantially eliminate transfer of thermal energy, and/or RF energy to tissue of the patient in contact with the shield. In one embodiment, the shield 100 is enabled for active cooling. In one embodiment, the shield 100 is enabled for active heating. In one embodiment, the shield 100 is configured with absorptive materials to absorb the energy and convert it to heat. In one embodiment, a shield 100 comprises thermally conductive materials that pulls the heat away from the tissue surface and dissipate the heat away from the main part of the shield 100. In one embodiment, a multilayer design can comprise thermally conductive materials to remove heat from the shield 100. In one embodiment, a multilayer design can comprise thermally insulative materials to keep heat away from tissue. In one embodiment, the shield 100 is enabled for both active cooling and active heating. Active cooling of the shield 100 can protect non-target region 30 from thermal energy and/or heating of shield 100 by emitted energy 12.

In one embodiment, materials 115, 125, 135, 155 are configured to reflect emitted energy 12 (e.g., ultrasound energy). In one embodiment, materials 115, 125, 135, 155 are configured to substantially cancel emitted energy 12 (e.g., ultrasound energy). In one embodiment, materials 115, 125, 135, 155 are configured to refract emitted energy 12 (e.g., ultrasound energy). In one embodiment, materials 115, 125, 135, 155 are configured to scatter emitted energy 12 (e.g., ultrasound energy). In one embodiment, materials 115, 125, 135, 155 are configured to absorb emitted energy 12 (e.g., ultrasound energy).

In various embodiments, the acoustic impedance of the shield 100 is configured to reduce or eliminate transmission of ultrasound energy to a non-target region 30. Acoustic impedance is a material property Z with units ($M \times L^{-2} \times T^{-1}$; $N \times s/m^3$; or $Pa \times s/m$). Acoustic impedance is the product of material density multiplied by the longitudinal wave speed, or sound speed in the material:

$$Z = \rho \times V$$

where $\rho$ is the density of the medium ($M \times L^{-3}$; $kg/m^3$), and where V is the longitudinal wave speed or sound speed ($L \times T^{-1}$; m/s).

When ultrasound energy travels between two or more materials 115, 125, 135, 155, one form of emitted wave energy 12 can be transformed into another form. For example, when a longitudinal wave hits an interface at an angle, some of the energy can cause particle movement in the transverse direction to start a shear (transverse) wave. Mode conversion occurs when a wave encounters an interface between materials of different acoustic impedances and the incident angle is not normal to the interface. A mode conversion occurs every time a wave encounters an interface at an angle, resulting in reflection or refraction of ultrasound energy between two or more layers 110, 120, 130, 150. When ultrasound energy waves pass through an interface between two or more materials 115, 125, 135, 155 having different acoustic velocities, refraction takes place at the interface. The larger the difference in acoustic velocities between the two or more materials 115, 125, 135, 155, the more the ultrasound energy is refracted or reflected. Thus, the greater the difference between the relative acoustic impedance between materials or layers in the shield 100, the more the shield 100 protects or diverts emitted energy 12 from non-target region 30.

The characteristic acoustic impedance of air at room temperature is about 420 Pa×s/m. By comparison the sound speed and density of water are much higher, resulting in an acoustic impedance of roughly 1.5 MPa×s/m, about 3,400-3,700 times higher than air. While air has an impedance of roughly 420 Pa×s/m, various relative acoustic impedance levels can be calculated with respect to air. Acoustic impedance levels can be calculated for any material, but to illustrate differences in acoustic impedance levels, FIG. 3 lists acoustic impedance of various materials in relative terms on a scale normalized to the acoustic impedance of air. As illustrated in FIG. 3, water has an acoustic impedance that is roughly 3,700 times higher than air. Aluminum has an acoustic impedance that is roughly 42,000 times higher than air. Glass has an acoustic impedance that is roughly 47,000 times higher than air. Gold has an acoustic impedance that is roughly 156,500 times higher than air. Polyethylene has an acoustic impedance that is roughly 4,250 times higher than air. Silver has an acoustic impedance that is roughly 95,000 times higher than air. Steel has an acoustic impedance that is roughly 115,000 times higher than air. Stainless steel has an acoustic impedance that is roughly 113,500 times higher than air. Tungsten has an acoustic impedance that is roughly 252,000 times higher than air. In some embodiments, the shield 100 comprises one or more adjacent layers of materials that have an acoustic impedance that differ by a magnitude of at least 1,000. In some embodiments, the shield 100 comprises one or more adjacent layers of materials that have an acoustic impedance that differ by a magnitude of at least 10,000. In some embodiments, the shield 100 comprises one or more adjacent layers of materials that have an acoustic impedance that differ by a magnitude of at least 100,000. Air is used in some embodiments, but not used in others. In some embodiments, the shield 100 comprises one or more adjacent layers of materials that have an acoustic impedance that differ by a magnitude of at least 250,000. In some embodiments, the shield 100 comprises one or more adjacent layers of materials that have an acoustic impedance that differ by a magnitude of at least 1,000,000. For example, the shield 100 may comprise one or more adjacent layers of stainless steel and polyethylene. In various embodiments, the shield can comprise any one or combination of the materials listed at FIG. 3.

A vacuum, or lack of material or lack of air, can have an acoustic impedance level that approaches zero. Thus, the relative difference between any material when compared to air is further increased when compared to the near zero acoustic impedance of a vacuum. In one embodiment, one or more layers of the shield has an acoustic impedance, as normalized to the acoustic impedance of air, of zero, less than 1, less than about 10, less than about 100, or less than about 1,000. In some embodiments, the shield 100 comprises one or more adjacent layers of materials that have an acoustic impedance that differ by a magnitude of at least 10,000,000. In some embodiments, the shield 100 comprises one or more adjacent layers of materials that have an acoustic impedance that differ by a magnitude approaching infinity. In some embodiments, the shield 100 comprises one or more adjacent layers of materials that have an acoustic impedance that differ by a magnitude that is infinite.

In various embodiments, materials 115, 125, 135, 155 are configured to increase the acoustic impedance of the shield 100. In one embodiment, materials 115, 125, 135, 155 are configured to increase the relative difference in acoustic impedance between one or more material 115, 125, 135, 155 or one or more of the layers 110, 120, 130, 150 of the shield 100. In various embodiments, the relative difference of acoustic impedance values between any two materials 115, 125, 135 and 155 is at least a multiple or a factor of two, three, four, five, six through nine, ten, or more. In various embodiments, the relative difference of acoustic impedance values between any two adjacent materials 115, 125, 135, and 155 is a multiple or a factor in the range of 10-20; 20-50; 50-100; 100-500; 500-1,000; 1,000-10,000; 10,000-100,000; 100,000-1,000,000; 1,000,000-10,000,000; or 10,000,000 or more.

In various embodiments, one or more layers 110, 120, 130, 150 is configured for heating. In various embodiments, one or more layers 110, 120, 130, 150 is configured for cooling. In various embodiments, one or more layers 110, 120, 130, 150 is configured for sensing. In various embodiments, one or more layers 110, 120, 130, 150 is configured for sensing with one or more sensors. For example, one or more layers 110, 120, 130, 150 is configured for sensing a temperature of a portion of the shield 100, which can communicated to the procedure system 10 or communicated by a scale or numerical display on the shield 100. In various embodiments, one or more layers 110, 120, 130, 150 is configured for measuring. In various embodiments, one or more layers 110, 120, 130, 150 is configured with an active component.

In accordance with various embodiments, a shield 100 is configured to protect and/or shield various non-target regions 30, such as body parts, tissues, organs, implants, medical devices, and/or material in situ in the patient's body from high levels of acoustic energy during ultrasound treatment (e.g., cosmetic enhancement), and/or imaging procedures with an ultrasound transducer that are intended for affecting target tissue 20 with the transmission of ultrasound energy 12. In some embodiments, the shield 100 is configured to fit over a procedure recipient's eye, mouth, nose, ear or other body part to protect and/or shield the non-target region 30 from high levels of acoustic energy during an ultrasound treatment and/or imaging procedure intended to treat, enhance, and/or image tissues surrounding the orifices. In some embodiments, the shield 100 is configured to protect and/or shield non-target region 30 from ultrasound energy and a photon based energy emitted during a cosmetic enhancement procedure. For example, the shield 100 can be positioned to protect and/or shield non-target region 30 from energy emitted by an ultrasound transducer and energy emitted by a laser.

Figure 4:
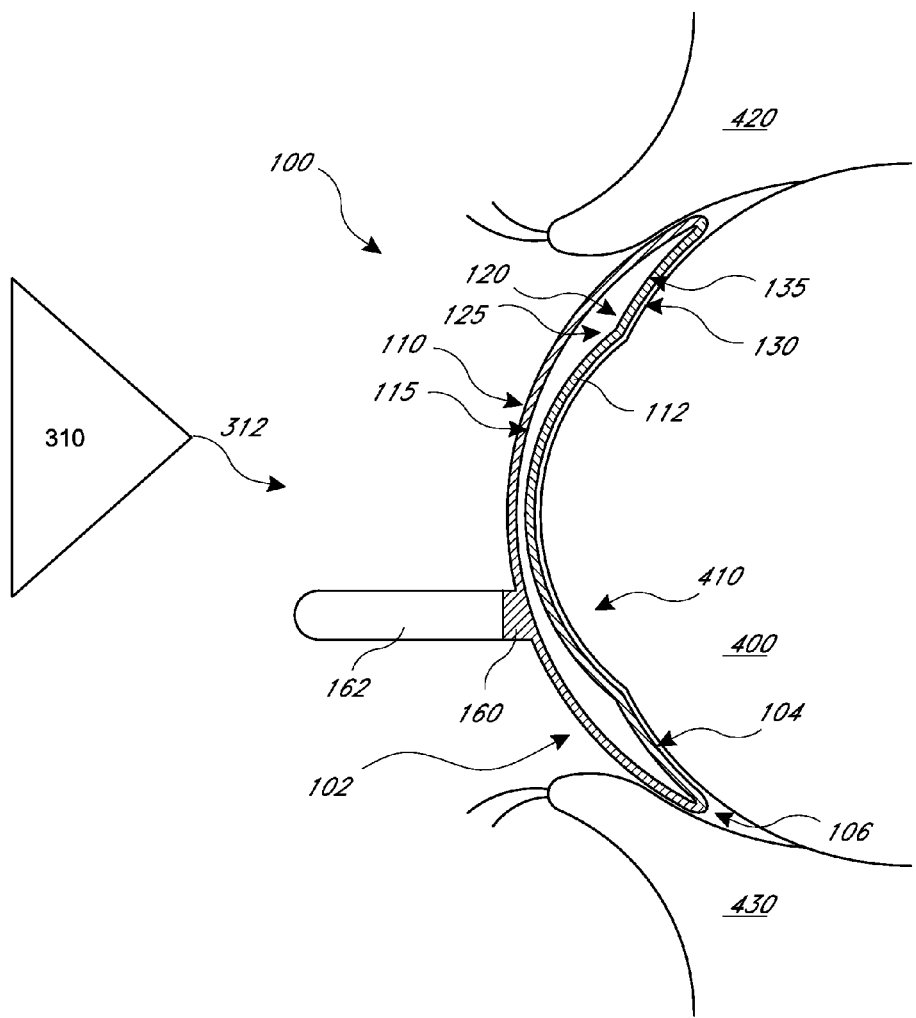
FIG. 4 is a schematic, partial cross-sectional side view of a multi-layered eye shield configured to fit over the eye and underneath the eyelids with an optional manipulation device according to one embodiment of the present invention.
Figure 5:
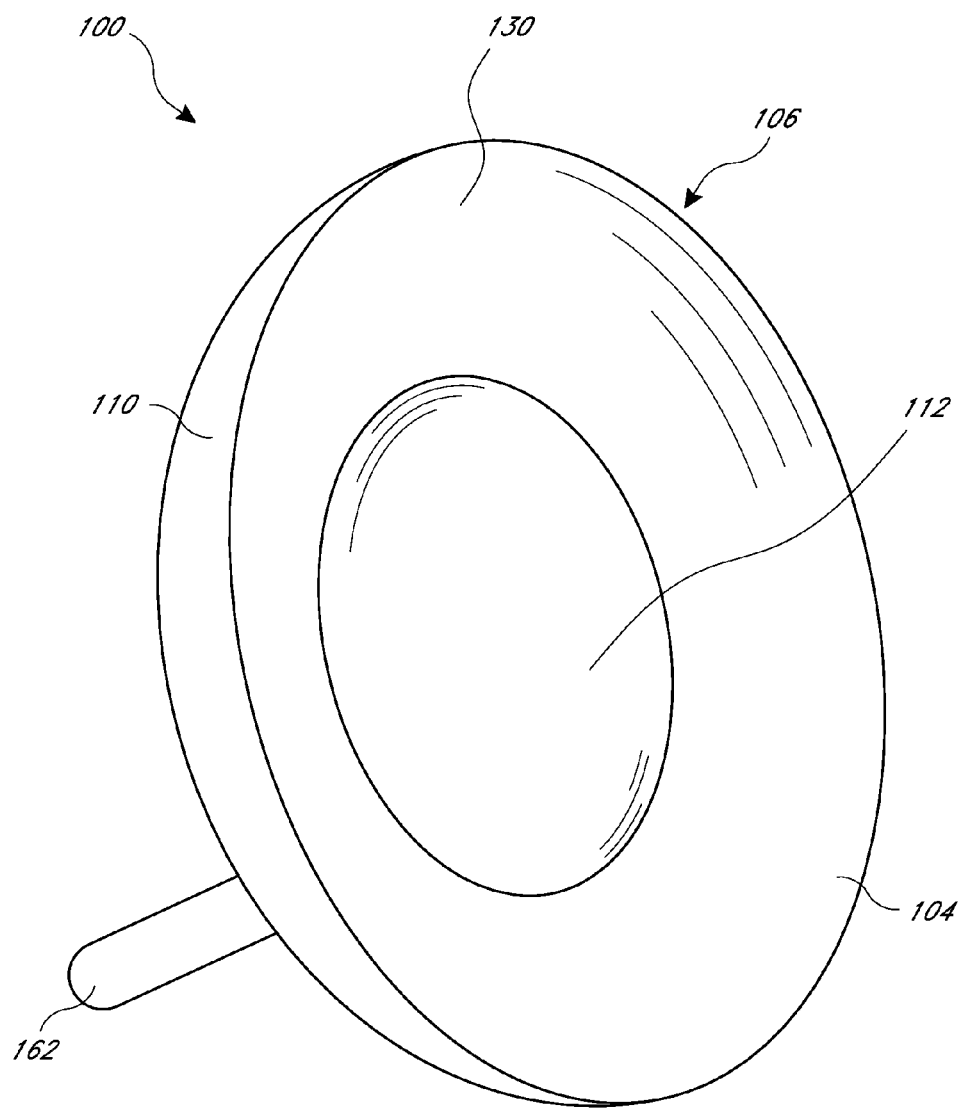
FIG. 5 is a schematic, perspective view of the multi-layered eye shield of FIG. 4.
Figure 6B:
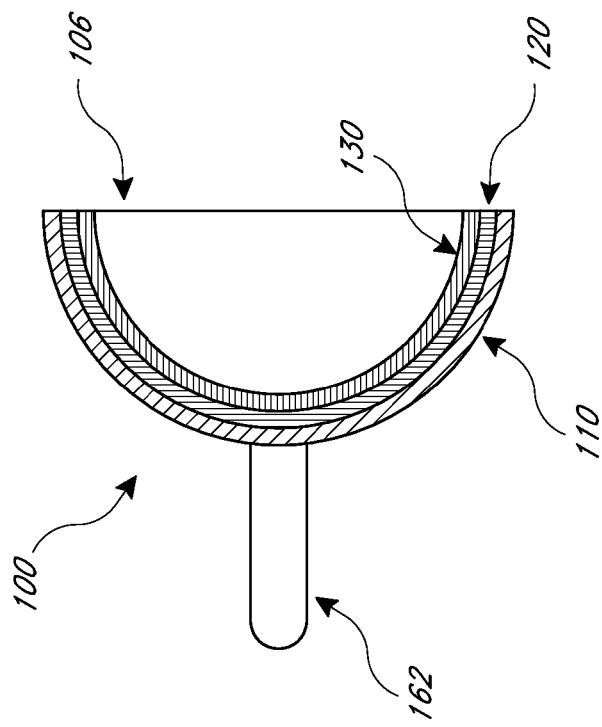
FIG. 6B is a schematic, partial cross-sectional side view of the eye shield of FIG. 6A.
Figure 6A:
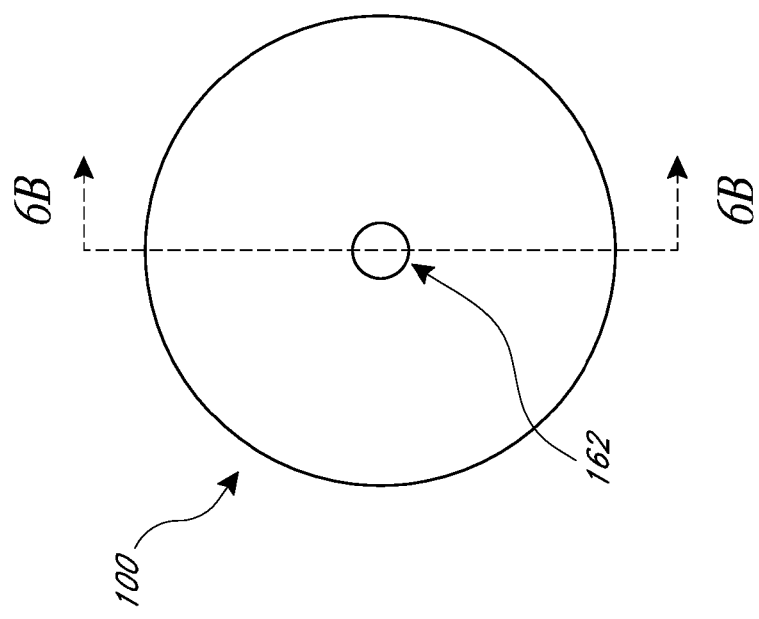
FIG. 6A is a schematic front view of an eye shield with an optional removable manipulation device according to one embodiment of the present invention.

As illustrated at FIG. 4, in accordance with various embodiments, a shield 100 is configured to protect a non-target region 30 that is an eye 400. In some embodiments, the shield 100 is configured to fit over an eye 400 to shield and/or protect the eye 400 from potentially damaging levels of acoustic energy during therapeutic ultrasound treatment (e.g., cosmetic enhancement) and/or imaging procedures intended to treat, and/or enhance, and/or image certain target tissues 20, or body parts, organs, implants, and/or material in situ in the body of a procedure recipient, such as a treatment recipient or patient. The eye 400 includes a cornea 410 that projects outward in a dome shape from the roughly spherical shape of the eye 400. The upper eyelid 420 and lower eyelid 430 are positioned around the eye 400. In various embodiments, the target tissue 20 can be the upper eyelid 420, the lower eyelid 430, or any region on, near or around the upper or lower eyelids 420, 430. When the upper eyelid 420 and lower eyelid 430 are closed, they at least partially enclose or surround the eye 400. A caruncula lacrimalis (not illustrated) is positioned between the eye and nose, and can be recognized as a soft tissue bulge between the upper eyelid 420 and lower eyelid 430 near the nose. Various muscles and tendons (not illustrated) are located around the eye 400.

In one embodiment, the shield 100 is configured to fit over an eye 400 and is sufficiently thin to fit under an upper eyelid 420, a lower eyelid 430, or both. In one embodiment, the shield 100 is configured to cover and/or contact a portion of an eye 400. In one embodiment, the shield 100 is configured to cover and/or contact a portion or the whole cornea 410. In one embodiment, the shield 100 is configured with one or more domes or indentations 112 in one or more layers to create a space and/or cavity over a portion of and/or the entire cornea 410. In one embodiment, the shield 100 is configured to cover and/or contact a portion of the sclera, or white part of the eye 400. In one embodiment, the shield 100 comprises a medicant, such as for example, a medicant, which can numb at least a portion of the eye 400, a medicant, which can protect a portion of the eye 400, a medicant, which can maintain and/or increase moisture in the eye 400, or combinations thereof. In one embodiment, the shield 100 comprises a source of saline solution in communication with a portion of the eye 400.

In various embodiments, the shield 100 is configured to be rigid, stiff, pliable, compliant, moldable, and/or flexible. In various embodiments, the shield 100 is configured to be gas permeable and/or gas impermeable. In various embodiments, the shield 100 is configured to fit the only the right eye or only the left eye and/or both eyes. In various embodiments, the shield 100 is configured to fit with the upper eyelid 420, a lower eyelid 430, caruncula lacrimalis, tendons and/or muscles around the eye 400.

In various embodiments, the shield 100 includes one or more layers 110, 120, 130, 150 as described in various embodiments herein. In various embodiments, the shield 100 includes an anterior surface 102 in contact with the upper eyelid 420, the lower eyelid 430, or both. In various embodiments, the shield 100 includes a posterior surface 104 adjacent the eye 400. In various embodiments, the shield 100 includes one or more edges 106. In some embodiments, one or more shield 100 surfaces 102, 104, faces, sides, and/or edges 106 are polished. In various embodiments, the shield 100 may comprise one, two, three, four, five, six, seven, eight, nine, ten, more than ten, twenty, fifty, less than one-hundred, one-hundred, or more layers, each layer made of a material. In one embodiment, the posterior surface 104 comprises a medicant, such as for example, a medicant that numbs at least a portion of the eye 400, a medicant that maintains and/or increase moisture in the eye 400, or combinations thereof. In one embodiment, the posterior surface 104 comprises a source of saline solution in communication with a portion of the eye 400. In one embodiment, the posterior surface 104 can be hydrophilic. In one embodiment, the posterior surface 104 comprises a video display. In one embodiment, the anterior surface 102 comprises a display configured to communicate a condition of the shield 100.

FIGS. 5, 6A and 6B, 7A and 7B, and 8A and 8B illustrate various embodiments of a shield 100. In one embodiment, shield 100 comprises or consists of a first layer 110 made of a first material 115, which is adjacent and connected to a second layer 120 made of second material 125. In one embodiment, the shield comprises a third layer 130 made of third material 135, which is adjacent and connected to a second layer 120 made of second material 125. In various embodiments, the shield 100 can comprise any number of additional adjacent, connected layers 150 made of any number of materials 155 are also present, depending on the total number of layers in the shield 100. In various embodiments, the layers 110, 120, 130, 150 can be connected, attached, glued, adhered, painted, bonded, electronically dispersed and/or machined together. In various embodiments, layers may contact other layers with one or more layers in between. In one embodiment, a first layer 110 contacts a third layer 130, with a second layer 120 in between. In one embodiment, a first layer 110 contacts a third layer 130, with a second layer 120 in between along one or more edges 106. In one embodiment, a second layer 120 can be sealed between a first layer 110 and a third layer 130. The layers 110, 120, 130, 150 can comprise same or different materials 115, 125, 135, 155, characteristics, and/or properties.

In one embodiment, the shield 100 comprises two or more layers configured as a contact lens for covering the cornea. In one embodiment, the shield 100 comprises two or more layers configured as a large contact lens for covering the cornea and at least a portion of the sclera. In one embodiment, the shield 100 comprises two or more layers configured as a contact lens for covering the cornea and the visible sclera when the eyelids 420, 430 are open on the eye 400. In one embodiment, the shield 100 is gas permeable.

In one optional embodiment, the shield 100 includes a manipulation device 162. In various embodiments, the manipulation device 162 is permanently, temporarily, or removably attachable to the anterior surface 102 of an outer layer. In various embodiments, the manipulation device 162 is configured to assist in placement, implantation, movement, and/or removal of the shield 100 from the body. In various embodiments, the manipulation device 162 is a handle and/or other similar gripping device to aid in the placement and removal of the shield 100. In one embodiment, the manipulation device 162 is selectively attachable and detachable to the shield 100 at a manipulation device interface 160.

In various embodiments, the manipulation device 162 is be positioned anywhere on the shield 100. In various embodiments, the manipulation device 162 is positioned near or against the lower eyelid 430 below the cornea 410, enabling the upper eyelid 420 to close with minimal engagement with the manipulation device 162, thereby reducing potential movement of the shield 100. In various embodiments, the manipulation device 162 is configured to be placed and/or removed using suction type devices, fingers and/or tweezers, a latch, a lock, a thread, a snap fit, a peg, a lever, an interface, magnetism, adhesive, hook and loop, or other attachment means or mechanism. In various embodiments, the manipulation device 162 is configured to be removable or detachable. In various embodiments, the shield 100 optionally includes one or more small relief holes, channels and/or grooves to aid in the placement and/or removal of the shield 100 from the eye 400. The shield 100 can also be configured to have a detachable manipulation device interface 160.

In accordance with one embodiment for a method of protecting and/or shielding a non-target region 30 from acoustic energy 12 during a procedure, the method includes interposing a shield 100 between an ultrasound procedure system 310 and the non-target region 30 that is not intended to be enhanced and/or treated and/or imaged by ultrasound and/or various other treatment and/or imaging procedures. In one embodiment, the ultrasound procedure system 310 emits ultrasound energy 12 to affect a target tissue 20. In one embodiment, the shield 100 is removed once the ultrasound procedure system 310 completes its emission of ultrasound energy 12 to affect the target tissue 20.

In various embodiments, a method of shielding the eye 400 from an emission of ultrasound energy 12 in a cosmetic enhancement procedure to the area around an eye 400 includes the steps of positioning a shield 100 between an eyelid 420, 430 and an eye 400 and applying ultrasound energy 12 from a transducer to tissue proximate the upper eyelid 420 and the lower eyelid 430. In some embodiments, the shield 100 includes a first layer 110 with a first material 115 with a first acoustic impedance, a second layer 120 with a second material 125 with a second acoustic impedance, and a third layer 130 with a third material 135 having a third acoustic impedance. In some embodiments, the second layer 120 is in contact with and adjacent to the first layer 110. In some embodiments, the third layer 130 is in contact with and adjacent to the second layer 120. In various embodiments, the first acoustic impedance is at least ten, hundred, thousand, ten thousand, one hundred thousand or more times the second acoustic impedance. In various embodiments, the third acoustic impedance is at least ten, hundred, thousand, ten thousand, one hundred thousand or more times the second acoustic impedance. In some embodiments, the first layer, the second layer and the third layer are configured to reduce acoustic transmission to the eye 400.

In various embodiments, a method of shielding a non-targeted region 30 of a body from undesired emission of energy 12, 12 includes the steps of positioning a shield 100 between a non-targeted region 30 of the body a source of the energy 12, 12 and applying the energy 12, 12 to tissue proximate the non-targeted region 30 of the body. In one embodiment, the shield 100 includes a first layer 110 with a first acoustic impedance, a second layer 120 with a second acoustic impedance, and a third layer 130 with a third acoustic impedance. The second layer 120 is in contact with the first layer 110 and the third layer 130. The first acoustic impedance and the third acoustic impedance are at least one thousand times the second acoustic impedance. The first layer 110, the second layer 120 and the third layer 130 are configured to reduce application of the energy 12, 12 to the non-targeted region 30 of the body. In various embodiments, the undesired energy 12 comprises ultrasound energy 12, or comprises a combination of ultrasound energy 12 and at least one other energy. In one embodiment, the method also includes applying energy 12 from a transducer to tissue proximate the upper eyelid 420 and the lower eyelid 430. In one embodiment, the method can further include applying the energy 12, 12 from a transducer to perform a cosmetic enhancement procedure, such as, for example, a face lift, a rhinoplasty procedure, or a blepharoplasty procedure.

In various embodiments, a method of shielding an eye from ultrasound energy in a cosmetic enhancement procedure to the area around the eye, includes the steps of positioning a shield 100 between a portion of the eye, and a ultrasound source then applying ultrasound energy from the ultrasonic transducer to target tissue proximate to the eye, and shielding the portion of the eye from the ultrasound energy. In one embodiment, the shield 100 comprises a plurality of layers having a plurality of acoustic impedances, wherein at least one of the plurality of layers comprises an acoustic impendence of at least 10,000 times greater than an acoustic impendence of an adjacent layer. In one embodiment, the plurality of layers comprise a first layer comprising a first acoustic impedance, a second layer in contact with the first layer, and comprising a second acoustic impedance being at least ten thousand times less than the first acoustic impedance, and a third layer comprising a third material in contact with the second layer and comprising a third acoustic impedance being at least ten thousand times greater than the second acoustic impedance. In one embodiment, the method can include the step of applying a second energy to the target tissue proximate to the eye; and shielding the portion of the eye from the second energy. In one embodiment, the second energy is a photon-based energy. In one embodiment, a source of the second energy is a laser.

In one embodiment, a shield 100 includes material with an impedance that is similar to, or not significantly different from a tissue impedance. In one embodiment, a shield 100 material does not have a large impedance when compared to tissue. In one embodiment, a shield 100 material is matched to tissue so reflections of energy 12 are not immediately created that may cause a secondary lesion to form or add to the already distributed energy at the focus from the forward propagation of the energy 12 from a procedure system 10. This material although matched to tissue, or in one embodiment, water, would 'catch' the impinging acoustic energy 12 and have a high enough attenuation to stop it before it hits the eye or other tissue. In one embodiment, a shield 100 has a specific heat that is high enough such that the temperature rise of such a material upon absorbing energy 12 would be reduced, or minimal. In various embodiments, a shield is configured to reach not more than a maximum temperature when energy is directed to the shield. In some embodiments, a maximum temperature of a shield is 60° C., 50° C., 45° C., 43° C., 40° C., or less.

In various embodiments, a method of shielding a non-targeted region of a body from an emission of energy includes the steps of positioning a shield 100 between a non-targeted region of the body a source of emission of energy, emitting the energy into target tissue proximate to the non-targeted region of the body, and blocking the energy transmission from the non-targeted region of the body. In one embodiment, the shield 100 comprises at least two adjacent layers comprising acoustic impedance differing by a factor of at least 10,000. In one embodiment, the method can include the step of cosmetically enhancing a portion of the target tissue. In one embodiment, the energy is ultrasonic energy and at least one other energy. In one embodiment, the at least one other energy comprises a photon-based energy. In one embodiment, the method can include applying energy from an ultrasonic transducer to target tissue proximate the upper eyelid and the lower eyelid. In one embodiment, the method can include applying energy from an ultrasonic transducer for blepharoplasty.

In various embodiments, a shield 100 configured for selectively protecting tissue from at least two energy sources, comprising a first layer, which comprises a first material with a first impedance and a second layer in contact with and adjacent to the first layer, the second layer comprises a second material with a second impedance. In one embodiment, the first impedance is at least ten thousand times greater than the second impedance. In one embodiment, the first layer and the second layer are configured to reduce transmission to a non-target region in a body of a subject, and at least one of the first layer and the second layer is configured to at least one of the at least two energy sources. In one embodiment, at least two energy sources are an ultrasound energy source and a photon-based energy source. In one embodiment, at least one of the first layer and the second layer is configured to block a photon-based energy. In one embodiment, one of the first layer and the second layer is opaque to a photon-based energy.

In one embodiment, a shield 100 is attached to the procedure system 10 ensure proper alignment for a procedure. In various embodiments, the shield 100 can be attached, locked, temporarily connected, adhered, interfaced, and/or aligned with the procedure system 10.

In various embodiments, a shield 100 can comprise highly absorptive materials with a reasonably high specific heat and/or thermally conductive and non-thermally conductive layers. In some embodiments, a shield 100 uses reflection to redirect energy 12. In some embodiments, a shield 100 absorbs the energy 12 and converts it to another form. In one embodiment, a shield 100 absorbs the energy 12 and converts it to heat. In one embodiment, a shield 100 material may have an absorption coefficient of nearly 50 dB per cm at 5 MHz. Although absorption can attenuate the energy beam 12, one challenge is controlling the temperature rise in the shield 100 upon absorption of part of the energy. In various embodiments, the rise in temperature can be mitigated by choosing materials with high specific heats or diverting the heating that occurs in the acoustic block. If not dissipated properly, the shield 100 material may heat up, causing pain, discomfort, damage, and/or burns to a tissue. In one embodiment, a shield 100 comprises thermally conductive materials that pulls the heat away from the tissue surface and dissipate the heat away from the main part of the shield 100. In one embodiment, a multilayer design can comprise thermally conductive materials to remove heat from the shield 100. In one embodiment, a multilayer design can comprise thermally insulative materials to reduce the transmission of heat from the shield 100 to tissue.

In several embodiments of the invention, the shield 100 is configured for placing under an eyelid 420, 430. The shield may be round, oval, elliptical, or oblong. The shield, in some embodiments, has a width of about 5 mm to about 20 mm, a length of about 5 mm to about 20 mm, and a thickness of about 0.2 mm to about 3 mm. Other dimension measurements are also used within the eye 400. In one embodiment, the shield 100 is dimensioned to shield only portions of the eye 400, and can be shaped and dimensioned similar to a contact lens. In yet other embodiments, the shield 100 is dimensioned to shield the entire eye 400. The shield 100 may or may not be configured to contact the eye 400. For ocular embodiments, the shield can be coated with (or otherwise contain) lubricating drops or other features that enhance patient comfort.

In non-ocular embodiments, dimensions are adapted to the target area. For example, the shield 100 can have a length and/or width that is between about 2 cm-48 cm, or larger. Shield 100 shapes can further include rectangular, square, triangular or can have an amorphous appearance. In some embodiments, the layered materials disclosed herein can be used to construct protective clothing-like constructs (including, but not limited to, vests and aprons).

In some embodiments, the shield 100 is configured for blocking or redirecting post-focal energy 12 from reaching a non-target region 30. In some embodiments, the shield 100 is configured to re-radiate the energy 12 and create a focus from a secondary reflection. In some embodiments, a shield 100 is configured to re-radiate the energy 12 and create a focus from a secondary reflection with one or more surface features 170. In one embodiment, a surface feature 170 is a facet. In one embodiment, a surface feature 170 is a contour. In various embodiments, the shape and/or material of a surface feature 170 redirects energy 12 and focuses and/or disperses the energy 12 away from the non-target region 30. In one embodiment, a concave surface feature 170 redirects energy 12 to a focus in a location directed away from a non-target region 30. In one embodiment, a convex surface feature 170 redirects energy 12 to a focus in a location directed away from a non-target region 30. In various embodiments, two or more surface features 170 can be positioned or aligned in such a way to further disperse or redirect energy 12.

In some embodiments, a shield 100 has a surface finish configured for high reflection and/or scattering coefficients. In some embodiments, a shield 100 has a surface finish that increases the reflection coefficient by producing air pockets between the shield 100 and tissue. In one embodiment, an eye shield 100 has a surface finish with one or more features 170 that increase the reflection coefficient by producing air pockets between the eye shield and eye lid as well as the eye shield and eye ball.

In one embodiment, a partially focused wave or plane wave radiation from the procedure system 10 would reflect off one or more features 170 of the shield 100 and focus at a location different from the non-target region 30. In one embodiment, a partially focused wave or plane wave radiation from the procedure system 10 would reflect off one or more features 170 of the shield 100 and focus at a target tissue 20. In one embodiment, use of reflected energy off a shield 100 can significantly reduce the blocking requirements of a shield 100. In one embodiment, a partially focused wave or plane wave radiation from the procedure system 10 would reflect off one or more features 170 of an eye shield 100 and focus at a target tissue 20 in an intended depth in an eyelid. In one embodiment, post focal energy is directed toward the device 10 and not the patient. In one embodiment, post focal energy is directed away from a non-target region 30. In one embodiment, post focal energy is directed toward target tissue 20.

Figure 9A:
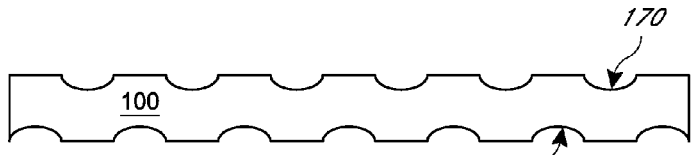
FIGS. 9A-9D are schematic, cross-sectional side views of shields according to embodiments of the present invention.
Figure 9B:
Figure 9C:
Figure 9D:
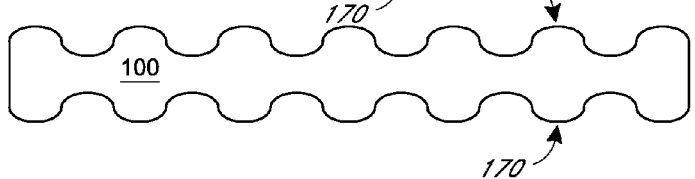

As shown in FIGS. 9A-10D, various embodiments of shields 100 with a plurality of features 170 can be used to improve scattering, attenuation and/or overall blocking ability. In some embodiments, concave and/or convex features 170 are on one, two, or more sides of a shield 100. In some embodiments, features 170 can be in the same or different planes. FIGS. 9A-9D illustrate an embodiment with a plurality of features 170 in the same plane, such that the cross section shows features 170 on two or more sides of a shield 100 that are aligned in a same plane (e.g. a plane that is parallel to the cross-sectional view). FIG. 9A illustrates one embodiment of a shield 100 with a plurality of concave features 170. FIG. 9B illustrates one embodiment of a shield 100 with a plurality of convex features 170. FIG. 9C illustrates one embodiment of a shield 100 with a plurality of concave and convex features 170 arranged in an in-phase configuration. FIG. 9D illustrates one embodiment of a shield 100 with a plurality of concave and convex features 170 arranged in an out-of-phase configuration.

Figure 10A:
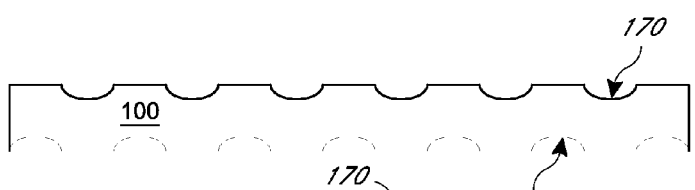
FIGS. 10A-10D are schematic, cross-sectional side views of shields according to embodiments of the present invention.
Figure 10B:
Figure 10C:
Figure 10D:

FIGS. 10A-10D illustrate an embodiment with a plurality of features 170 in different planes, such that the cross section shows features 170 and 172 on two or more sides of a shield 100 that are not aligned in a same plane (e.g. features 170 and 172 are not in the same plane that is parallel to the cross-sectional view). FIG. 10A illustrates one embodiment of a shield 100 with a plurality of concave features 170 that are in a first plane, and a plurality of concave features 172 that are in a second plane, the second plane different from the first plane. FIG. 10B illustrates one embodiment of a shield 100 with a plurality of convex features 170, 172. FIG. 10C illustrates one embodiment of a shield 100 with a plurality of concave and convex features 170, 172 arranged in an in-phase configuration. FIG. 10D illustrates one embodiment of a shield 100 with a plurality of concave and convex features 170, 172 arranged in an out-of-phase configuration. As indicated by the broken lines in the illustrations at FIGS. 10A-10D, certain features 170 and 172 are not in the same plane.

FIG. 11 illustrates various embodiments of a shield from a top view showing a number of features 170 and 172 that are arranged in various configurations such that certain features 170 are in different alignments from other features 172.

In some embodiments, one or more features 170 on a shield 100 reduce or prevent acoustic coupling. In some embodiments, the size of a feature 170 would be on the order of a wavelength to produce a scattering effect. In some embodiments, if the size of the feature 170 is larger than a wavelength, then each feature 170 acts more like a specular reflector. In various embodiments, features 170 may exist on one side, two, three, four, or more sides of the shield 100. The size, density and pattern of features 170 can be varied depending on the reflectivity requirements, wavelength used, and the possibility of moisture/water ingress into the pockets during treatment. In one embodiment, a shield 100 can include one or more features 170 that reduce and/or prevent moisture or water ingress during a procedure. Although various embodiments of feature 170 patterns can be aligned, it is also contemplated to have embodiments with random modifications to the surface finish that would also help increase the scattering or reduction of energy 12 transmission with respect to a non-target region 30.

In various embodiments, a shield 100 can de-focus an energy beam 12 that exits the shield 100. In one embodiment, a shield 100 comprises defocusing materials that further and more rapidly spread the energy 12. In one embodiment, if energy 12 is focused prior to the reflection off of the shield 100, then a top layer of the shield 100 may also be used to increase the overall spread of the reflection away from the non-target region 30.

In one embodiment, a shield 100 acts as an acoustic transmission line. In some embodiments, a shield 100 can use one or more materials that do not have a significant difference in impedance to tissue and still reduce acoustic transmission to safe levels. In one embodiment, for a shield 100 that approximates a lossless acoustic transmission line, the input impedance is given as:

$$Z_{in}(l) = Z_0 \frac{Z_L + jZ_0 \tan(\beta l)}{Z_0 + jZ_L \tan(\beta l)},$$

or $$Z_{in}(l) = Z_0 \times ((Z_L + jZ_0 \tan(\beta l))/(Z_0 + jZ_L \tan(\beta l))$$

where $Z_L$ is the load impedance where $Z_0$ is the characteristic impedance of the transmission line where $\beta$ is $2\pi/\lambda$ and where l is the thickness of the shield.

In one embodiment, a shield 100 has a thickness (l) that is a multiple of half a wavelength and the input impedance is just $Z_L$ which is the acoustic impedance of tissue. In this case, it is as though the acoustic transmission line or shield 100 is not even present. In one embodiment, a shield 100 has a thickness (l) is half a wavelength. In this case, the input impedance is:

$$Z_{in} = \frac{Z_0^2}{Z_L},$$

or $Z_{in} = Z_0\hat{\ }2/Z_L$ where $Z_L$ is the load impedance and where $Z_0$ is the characteristic impedance of the transmission line.

In one embodiment, although the characteristic impedance is roughly a factor of 2 different than water (e.g. 3 MRayls), the input impedance may be much higher, depending on the frequency and thickness. In one example, an embodiment of a shield is made of epoxy with an input effective impedance is 6 MRayls. In this case, the reflection coefficient is 60%, which is higher than the 33% predicted if the 3 MRayls was semi-infinite.

Figure 12:
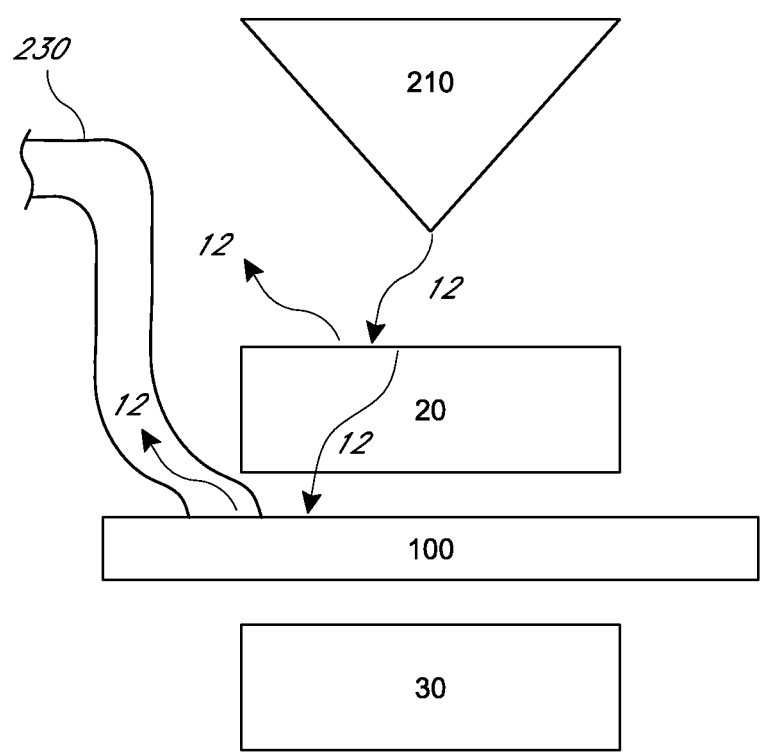
FIG. 12 is a schematic block diagram illustrating a shielding system with an energy diversion device according to various embodiments of the present invention.

FIG. 12 illustrates one embodiment of a shield 100 with an energy diversion device 230 that is configured to remove or dissipate energy 12, 12 that is absorbed by the shield 100. In some embodiments, acoustic energy 12 that is absorbed by the shield 100 is converted to heat. This heat can raise the temperature of the shield 100, causing discomfort or damage to any surrounding tissue. In some embodiments, the shield 100 includes an absorbing material with a high heat capacity, such that more energy is needed to raise the temperature of the absorbing material. In various embodiments, a shield 100 reduces the thermal conductivity to surrounding tissue by absorbing energy 12 with a high heat capacity, or by routing the heat away from the tissue through an energy diversion device 230. In various embodiments, the energy diversion device 230 is a heat conduit, a coolant channel, a heat exchanger, and/or a fluid circuit configured to draw excess heat or energy from the shield 100 and surrounding tissue.

In some embodiments, acoustic energy 12 that is absorbed by the shield 100 is converted to electrical energy. In some embodiments, acoustic energy 12 that is absorbed by the shield 100 is converted to electrical energy through a piezoelectric effect. In one embodiment, the shield 100 includes a piezoelectric sensor configured to absorb energy 12 and convert it in to an electrical signal. In various embodiments, the energy diversion device 230 is an electrical circuit.

In one embodiment, a shield 100 includes one or more acoustic sensors (piezoelectric) that may be used to give confirmation to a physician that energy 12 is being properly blocked, reduced, targeted, or aligned with the shield 100 with respect to target tissue 20 and/or a non-target region 30. In one embodiment, an acoustic sensor is a piezoelectric sensor. In one embodiment, one or more thermocouples may be added to and/or embedded in the shield 100 to monitor temperature, shield performance, heating, and/or proper positioning of the shield 100 with respect to target tissue 20 and/or a non-target region 30.

In various embodiments, a shield 100 can combine features or characteristics of any of the embodiments disclosed herein.

Example 1

The following example is intended to be a non-limiting embodiment of the invention.

Figures 13, 14:
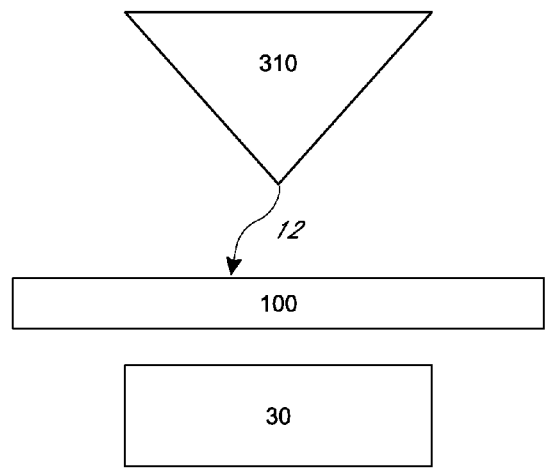
FIG. 13 is a schematic block diagram illustrating an experimental setup used to measure acoustic power transmission through an embodiment of a shield.
FIG. 14 is a chart illustrating results from the experiment setup in FIG. 13.

As illustrated at FIGS. 13 and 14, it was experimentally verified that an embodiment of a multi-layered shield 100, which was placed between various ultrasound procedure systems 310—and non-target region 30, reduced or eliminated the transmission of ultrasound waves 12 to a non-target region 30. In the experiment, the shield 100 was constructed of a multi-layer stack of stainless steel, air, and stainless steel with a total thickness 1.40 mm. The shield 100 had a first layer 110 made of first material 115 stainless steel, a second layer 120 made of second material 125 air, and a third layer 130 made of third material 135 stainless steel. The purpose of the experiment was to quantify the residual level of acoustic power that could pass from a superficial ultrasound transducer through a multi-layered stainless steel layers into a non-target region 30 with sensors to measure ultrasonic transmission. Two different ultrasonic transducers were utilized in the respective ultrasonic procedure systems 310, a 7.5 MHz-3.0 mm focal depth ultrasonic transducer and a 10.5 MHz-2.0 mm focal depth ultrasonic transducer. The shield 100 was mounted 0.5 mm away from the surface of the respective ultrasonic transducer 310 with hot melt adhesive at the periphery of the shield 100. Power with and without the shield 100 was measured three times and averaged.

Two measurement methods were utilized: a hydrophone (measuring pressure) and radiation force balance (measuring acoustic power). In both cases emitted energy 12 was measured with and without the stainless steel stack shield 100. Transmission loss was evaluated as the ratio of power with the shield 100 to without the shield 100. The results of the experiment summarized at FIG. 14 show acoustic power measurements with the shield 100 in both cases with both types of ultrasonic transducers having a residual power transmission of 0 watts, within measurement limits of 150 mW, representing over 100× attenuation (>20 dB) compared to the 16 watt incident power. Hydrophone measurements reveal extreme attenuation of over 56 dB down (2.5 parts per million) which is at the noise floor of measurements. Without the multi-layer shield 100 in place, 15.6 watts of acoustic power was transmitted to the sensor with the 7.5 MHz-3.0 mm focal depth ultrasonic transducer and 14.6 watts of acoustic power was transmitted to the sensor with the 10.5 MHz-2.0 mm focal depth ultrasonic transducer.

Additionally, as illustrated in FIG. 14, experimental hydrophone measurements revealed attenuation of over 56 dB down with the multi-layer shield 100 in place. The ultrasonic transducers 310 were placed facing upward in a degassed water bath at room temperature. The entire apparatus was slightly inclined so that any air bubbles in the ultrasonic transducers 310 stay out of the acoustic path. A Dapco needle hydrophone mounted in a 3-axis micrometer adjustable stage was used to monitor intensity. A FET probe and narrowband (300 Hz) spectrum analyzer were used to measure the hydrophone voltage. The FET probe had a gain of −20 dB. Dynamic range was limited to −56 dB. With no intervening shield 100, the peak intensity was located by iteratively adjusting the XYZ stage. The shield 100 was then placed between one ultrasonic transducer 310 at a time and the hydrophone. Fine adjustments were then made to hydrophone position to relocate the highest intensity.

In one embodiment, no power (0 watts or 0%) of the 15-16 watt incident power was detected, within the lower limit of measurement resolution (±0.15 watts). Thus, according to several embodiments of the invention, the shield 100 was able to block 100% of acoustic energy. In other embodiments of the invention, the shield 100 blocks at least 99%, 95%, 90%, 80%, 70% or 50% of undesired energy (including, but not limited to, ultrasound energy).

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

What is claimed is:

1. A biocompatible shield configured for selectively protecting tissue from acoustic energy comprising:
    a first layer,
       wherein the first layer comprises a first material with a first acoustic impedance and a first reflection coefficient of between 60-100%; and
    a second layer in contact with and adjacent to the first layer,
       wherein the second layer comprises a second material with a second acoustic impedance,
    wherein the first acoustic impedance is at least ten thousand times greater than the second acoustic impedance.

2. The shield of claim 1, wherein the first layer and the second layer are configured to reduce acoustic transmission to a non-target region in a body of a subject.

3. The shield of claim 1, wherein the shield is configured to be positioned within a subject's eye.

4. The shield of claim 1, wherein the shield is configured to be positioned between a subject's eye and a source of said acoustic transmission.

5. The shield of claim 1, further comprising a third layer comprising a third material in contact with and adjacent to the second layer, the third material having a third acoustic impedance.

6. The shield of claim 5, wherein the third acoustic impedance is at least ten thousand times greater than the second acoustic impedance.

7. The shield of claim 1, wherein the first acoustic impedance is at least one hundred thousand times the second acoustic impedance.

8. The shield of claim 1, wherein said shield comprises stainless steel.

9. The shield of claim 5 wherein the first material comprises stainless steel, the second material comprises air, and the third material comprises stainless steel.

10. The shield of claim 5, wherein the second layer is sealed between the first layer and the third layer and is under at least partial vacuum.

11. The shield of claim 1, wherein said shield is configured to fit over a portion of an eye and underneath at least one eyelid.

12. The shield of claim 1, further comprising a manipulation device to aid in the insertion and removal of said shield from the body of a patient.

13. The shield of claim 12, wherein the manipulation device comprises a tool that is coupled to said shield.

14. The shield of claim 1, further comprising one or more sensors configured to measure an amount of energy absorbed by the shield.

15. The shield of claim 1, further comprising an energy diversion device configured to remove or dissipate energy absorbed by the shield.

16. The shield of claim 1, further comprising one or more surface features comprise at least one of the group consisting of concave and convex features, the one or more surface features configured for a high reflection coefficient.

17. The shield of claim 16, wherein the one or more features produce an air pocket between the shield and tissue.

* * * * *